United States Patent
Lee et al.

(10) Patent No.: US 8,993,721 B2
(45) Date of Patent: Mar. 31, 2015

(54) PEPTIDES FOR TARGETING APOPTOTIC CELLS AND USES THEREOF

(75) Inventors: Byung Heon Lee, Daegu (KR); In San Kim, Daegu (KR)

(73) Assignee: Kyungpook National University Industry-Academic Cooperation Foundation

( * ) Notice: Subject to any disclaimer, the term of this patent is extended or adjusted under 35 U.S.C. 154(b) by 0 days.

(21) Appl. No.: 13/467,689

(22) Filed: May 9, 2012

(65) Prior Publication Data

US 2012/0316101 A1 Dec. 13, 2012

Related U.S. Application Data

(63) Continuation-in-part of application No. 12/465,007, filed on May 13, 2009, now Pat. No. 8,217,012.

(30) Foreign Application Priority Data

May 14, 2008 (KR) ........................ 10-2008-0044410

(51) Int. Cl.
| | | |
|---|---|---|
| C07K 7/06 | (2006.01) | |
| A61K 38/08 | (2006.01) | |
| A61K 47/48 | (2006.01) | |
| A61K 49/00 | (2006.01) | |
| A61K 38/00 | (2006.01) | |

(52) U.S. Cl.
CPC ........ *A61K 47/48246* (2013.01); *A61K 49/0032* (2013.01); *A61K 49/0043* (2013.01); *A61K 49/0056* (2013.01); *C07K 7/06* (2013.01); *A61K 38/00* (2013.01); *C07K 2319/33* (2013.01); *G01N 2510/00* (2013.01)
USPC ........ 530/329; 514/17.7; 514/19.2; 514/19.3; 514/19.4; 514/19.5; 514/19.6; 514/1.9; 514/21.8

(58) Field of Classification Search
CPC ...... C07K 7/06; C07K 2319/33; A61K 38/08; A61K 47/48246; A61K 49/0032; A61K 49/0043; A61K 49/0056
USPC .............. 530/329; 514/17.7, 19.2, 19.3, 19.4, 514/19.5, 19.6, 1.9, 21.8
See application file for complete search history.

(56) References Cited

U.S. PATENT DOCUMENTS

| | | | | |
|---|---|---|---|---|
| 5,595,756 | A | * | 1/1997 | Bally et al. .................... 424/450 |
| 7,482,117 | B2 | * | 1/2009 | Cargill et al. ................ 435/6.14 |
| 2003/0181383 | A1 | * | 9/2003 | Podolsky ........................ 514/12 |
| 2007/0020723 | A1 | * | 1/2007 | Bornancin ................... 435/69.1 |
| 2007/0061924 | A1 | * | 3/2007 | Eriksson et al. .............. 800/298 |

OTHER PUBLICATIONS

Sporn MB, Suh N, "Chemoprevention of cancer," Carcinogenesis, 2000, 21:(3): 525-530.*
Auerbach R, Akhtar N, Lewis RL, Shinners BL, "Angiogenesis assays: Problems and pitfalls," Cancer and Metastasis Reviews, 2000, 19: 167-172.*
Gura Trisha, "Systems for Identifying New Drugs Are Often Faulty," Science, 1997, 278: 1041-1042.*
Jain RK, "Barriers to Drug Delivery in Solid Tumors," Scientific American, 1994, 58-65.*
Neidle, Stephen, "Cancer Drug Design and Discovery," Elsevier/Academic Press, 2008: 427-431.*
Stroke from Merck manual from http://www.merckmanual.com/professional/sec17/ch221a.html, pp. 1-4. Accessed Aug. 12, 2011.*
Arteriosclerosis from Merck manual from http://www.merckmanual.com/professional/sec07/ch077b.html, pp. 1-5. Accessed Aug. 12, 2011.*
Myocardial Infarction from Merck manual from http://www.merckmanul.com/professional/cardiovascular_disorders/coronary_artery_disease/acute_coronary_syndromes_acs.html?qt=myocardial infarction&alt=sh, pp. 1-19. Accessed Oct. 16, 2013.*
SEQ ID No. 1003 from US Patent No. 7,482,117, 2009.*
EAW23009 from NCBI GenBank database, p. 1. Accessed Mar. 30, 2014.*

\* cited by examiner

*Primary Examiner* — Julie Ha
(74) *Attorney, Agent, or Firm* — Mintz Levin Cohn Ferris Glovsky and Popeo, P.C.; Kongsik Kim; Richard B. Emmons

(57) ABSTRACT

Described herein is an isolated polypeptide which is capable of specifically targeting apoptotic cells undergoing apoptosis and consists of the sequence (I): Cys-$X_1$-Val-Ala-Pro-$X_2$ (I), wherein $X_1$ is an amino acid with polar uncharged side chain and $X_2$ is an amino acid with positive charged side chain. The isolated polypeptide of the present invention may be useful for detecting apoptotic cells, as well as detecting and imaging apoptotic cells in tumor tissue, apoptotic myocardial cells in myocardial infarction tissue, apoptotic nerve cells in stroke tissue, and arteriosclerosis site; the polypeptide is useful for targeted drug delivery thereto.

15 Claims, 16 Drawing Sheets

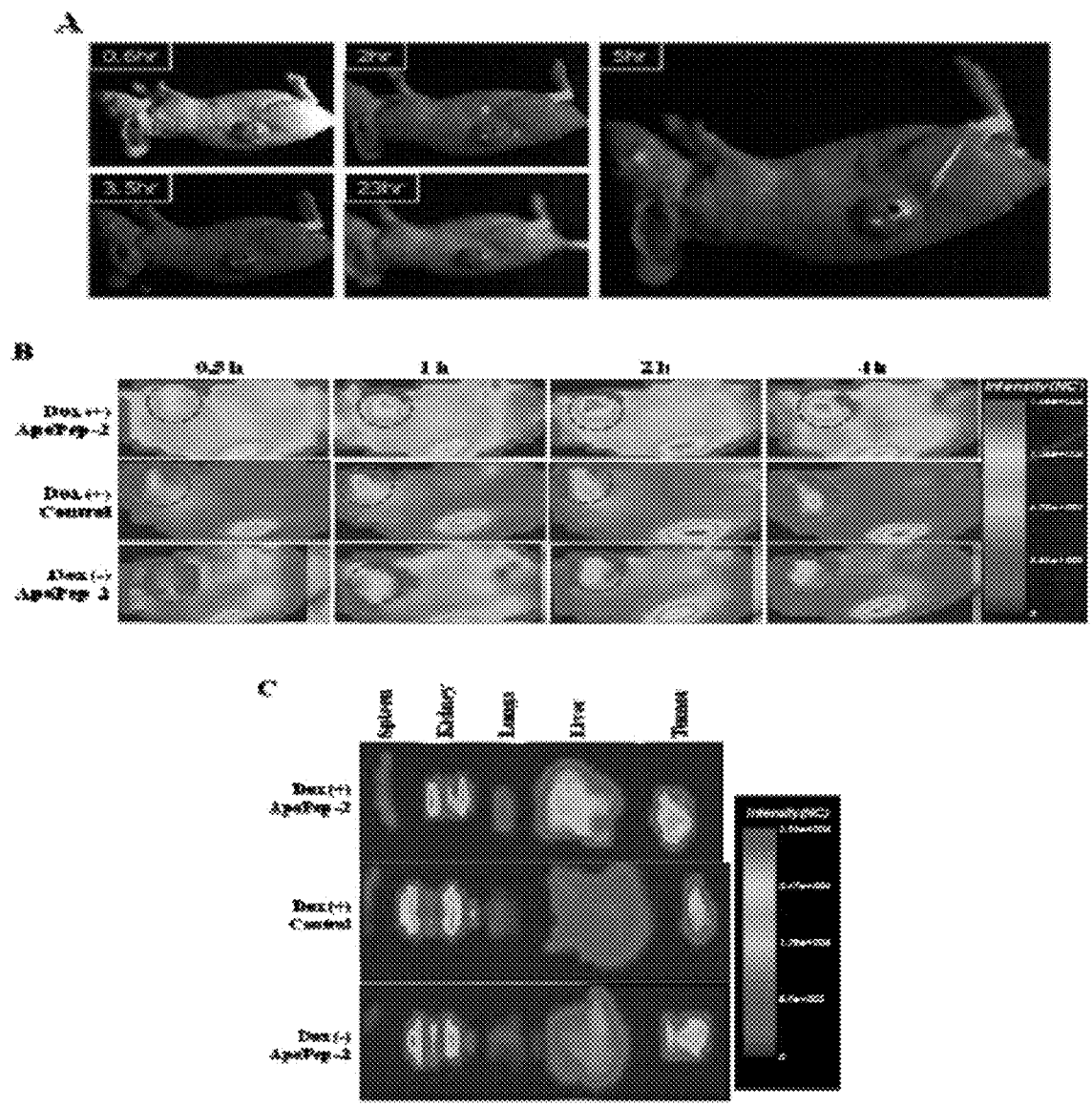

PEPTIDES FOR TARGETING APOPTOTIC CELLS AND USES THEREOF

CROSS-REFERENCE TO RELATED APPLICATION

This application is a continuation-in-part of U.S. Ser. No. 12/465,007, filed on May 13, 2009, which claims priority from Korean Patent Application No. 10-2008-0044410 filed on May 14, 2008, respectively in the Korean Intellectual Property Office. The disclosures of the priority applications, including the sequence listings and tables submitted in electronic form in lieu of paper, are incorporated by reference into the instant specification.

TECHNICAL FIELD

This application claims priority to Korean Patent Application No. 10-2008-0044410 filed on May 14, 2008, which is hereby incorporated by reference herein.

The present invention relates to peptides capable of specifically targeting apoptotic cells undergoing apoptosis and a use thereof. More particularly, it relates to an isolated polypeptide consisting of the sequence (I):

Cys-X1-Val-Ala-Pro-X2  (I)

wherein X1 is an amino acid with polar uncharged side chain and X2 is an amino acid with positive charged side chain and targeting apoptotic cells, a composition for detection of apoptotic cells comprising the same as an effective ingredient, a composition for drug delivery comprising the same as an effective ingredient, a composition for imaging comprising the same as an effective ingredient, and so on.

RELATED ART

Apoptosis is the process of programmed cell death resulting in the death of unnecessary or harmful cells during an organism's life cycle. In Greek, apoptosis means "to fall". It was named so by comparing the process of cell death to the falling of petals from a flower, and was first observed in 1972 by Kerr et al. (Kerr et al., *Br. J. Cancer,* 1972, 26:239-257). Apoptosis plays an important role in physiological events, including cell development, differentiation, immunity and the like (Meier et al., *Nature,* 2000, 407:796-801). Apoptosis is also important in several pathological conditions and diseases. For example, successful treatment with anticancer drugs involves apoptosis in the tumor tissue (Thomson, *Science,* 1995, 267:1456-1462). In contrast, decreased apoptosis results in formation of tumors. As another example, apoptosis of brain cells or myocardial cells occurs during stroke or myocardial infarction due to the shortage of blood supply to the brain or heart (Du et al, *J. Cereb. Blood Flow Metab.,* 1996, 16:195-201; Narula et al., *New Engl. J. Med.,* 1996, 335:1182-1189). In addition, apoptosis occurs frequently in organ transplant rejection or such diseases as autoimmune disease, degenerative cerebral nerve disorder, arteriosclerosis and viral infection (Thomson, *Science,* 1995, 267:1456-1462; Kageyama et al., *Ann. Thorac. Surg.,* 1998, 65:1604-1609).

Apoptosis is very important in clinical diagnosis and treatment. Therefore, imaging of apoptosis may be of great help to early diagnosis of degenerative cerebral nerve disorders (Alzheimer's disease, Parkinson's disease, etc.), monitoring of disease progression in myocardial infarction and stroke, monitoring of cancer therapeutic effect following anticancer drug treatment, decision of the possibility of rupture of atheromatous plaque, or the like, related with excessively increased apoptosis. Further, a selective delivery of a therapeutic or protecting agent to apoptotic cells may significantly improve therapeutic effect while reducing side effects.

One of the early events occurring in apoptotic cells is the change of the distribution of phospholipids that constitute the cell membrane. The most characteristic among them is the exposure of phosphatidylserine to outside of the cell membrane. Usually, phosphatidylserine is kept inside the cell membrane, but, when a cell receives an apoptotic signal or when a red blood cell ages, it is exposed to outside of the cell membrane (Fadeel, B. et al., *Cell Mol. Life. Sci.,* 2003, 60:2575-2585). A macrophage recognizes the exposed phosphatidylserine through a receptor on the cell surface and phagocytoses the apoptotic cell (Fadok, V. A. et al., *J. Immunol.* 1992, 148:2207-2216; Fadok, V. A. et al., *Nature* 2000, 405:85-90; Park, S. Y. et. al., *Cell Death Differ.,* 2008, 15:192-201). A large number of tumor cells show increased expression of phosphatidylserine outside the cell membrane (Utsugi, T. et al., *Cancer Res.* 1991, 15:3062-3066; Ran, S. et al., *Cancer Res.* 2002, 62:6132-6140; Woehlecke, H. et al., *Biochem. J.* 2003, 376:489-495). Further, the vascular endothelial cells in a tumor tissue expose phosphatidylserine outside of the cell membrane (Ran, S. et al., *Cancer Res.* 2002, 62:6132-6140; Zwaal, R. F. A. et al., *Blood.* 1997, 89:1121-1132). Therefore, in various situations especially including tumors, phosphatidylserine is deemed as a target material for diagnosis, treatment and treatment monitoring.

At present, the protein annexin V is generally used to detect phosphatidylserine on the surface of apoptotic cells. It is a 36 kDa protein and binds to phosphatidylserine with strong affinity (Vermes, I. et al., *Immunol. Methods.* 1995, 184:39-51). Although annexin V is a very useful targeting material or probe for in vitro application, its in vivo application is reported to be restricted because of, for example, slow removal out of the body due to large molecular weight (Vermeersch, H., et al., *Nucl. Med. Commun.* 2004, 25:259-263; Belhocine, T. Z. et al., *J. Proteome Res.* 2004, 3:345-349).

SUMMARY

The inventors of the present invention have worked to develop new proteins or fragments thereof capable of specifically and early targeting apoptotic cells in vivo. As a result, we have verified that a peptide having an amino acid sequence represented by anyone selected from the group consisting of SEQ ID NO: 1 to SEQ ID NO: 12 is capable of specifically targeting apoptotic cells, and completed the present invention.

Accordingly, an object of the present invention is to provide a peptide specifically targeting apoptotic cells and a use thereof.

To attain the object, in an aspect, the present invention provides a peptide having an amino acid sequence represented by anyone selected from the group consisting of SEQ ID NO: 1 to SEQ ID NO: 12 and specifically targeting apoptotic cells.

In another aspect, the present invention provides a polynucleotide encoding the peptide.

In another aspect, the present invention provides a composition for detection of apoptotic cells comprising the peptide as an effective ingredient.

In another aspect, the present invention provides a composition for drug delivery comprising the peptide as an effective ingredient.

In another aspect, the present invention provides a pharmaceutical composition for prevention and treatment of neoplastic disease comprising the peptide and an antitumor agent bound thereto as effective ingredients.

In another aspect, the present invention provides a composition for imaging neoplastic disease site comprising the peptide as an effective ingredient.

In another aspect, the present invention provides a pharmaceutical composition for treatment of stroke comprising the peptide and a nerve cell protecting agent bound thereto as effective ingredients.

In another aspect, the present invention provides a composition for imaging stroke site comprising the peptide as an effective ingredient.

In another aspect, the present invention provides a pharmaceutical composition for treatment of myocardial infarction comprising the peptide and a myocardial cell protecting agent bound thereto as effective ingredients.

In another aspect, the present invention provides a composition for imaging myocardial infarction site comprising the peptide as an effective ingredient.

In another aspect, the present invention provides a pharmaceutical composition for treatment of arteriosclerosis comprising the peptide and an anti-arteriosclerosis agent bound thereto as effective ingredients.

In another aspect, the present invention provides a composition for imaging arteriosclerosis site comprising the peptide as an effective ingredient.

In another aspect, the present invention provides a use of the peptide for detection of apoptotic cells.

In another aspect, the present invention provides a use of the peptide for drug delivery.

In another aspect, the present invention provides a method for drug delivery comprising administering the peptide and a drug bound thereto to a subject in need thereof at an effective dose.

In another aspect, the present invention provides a use of the peptide and an antitumor agent bound thereto for the preparation of an agent treating neoplastic disease.

In another aspect, the present invention provides a method for treatment of neoplastic disease comprising administering the peptide and an antitumor agent bound thereto to a subject in need thereof at an effective dose.

In another aspect, the present invention provides a use of the peptide and an antistroke agent bound thereto for the preparation of an agent treating stroke.

In another aspect, the present invention provides a method for treatment of stroke comprising administering the peptide and an antistroke agent bound thereto to a subject in need thereof at an effective dose.

In another aspect, the present invention provides a use of the peptide and an anti-myocardial infarction agent bound thereto for the preparation of an agent treating myocardial infarction.

In another aspect, the present invention provides a method for treatment of myocardial infarction comprising administering the peptide and an anti-myocardial infarction agent bound thereto to a subject in need thereof at an effective dose.

In another aspect, the present invention provides a use of the peptide and an anti-arteriosclerosis agent bound thereto for the preparation of an agent treating arteriosclerosis.

In another aspect, the present invention provides a method for treatment of arteriosclerosis comprising administering the peptide and an anti-arteriosclerosis agent bound thereto to a subject in need thereof at an effective dose.

In another aspect, the present invention provides a use the peptide for imaging a disease site selected from a group consisting of neoplastic disease, stroke, myocardial infarction and arteriosclerosis.

In another aspect, the present invention provides a method for imaging a disease site selected from a group consisting of neoplastic disease, stroke, myocardial infarction and arteriosclerosis comprising administering the peptide to a subject in need thereof at an effective dose.

The inventors of the present invention have worked to develop new proteins or fragments thereof capable of specifically and early targeting apoptotic cells in vivo. As a result, we have verified that an isolated polypeptide consisting of the sequence (I):

Cys-X1-Val-Ala-Pro-X2             (I)

wherein X1 is an amino acid with polar uncharged side chain and X2 is an amino acid with positive charged side chain is capable of specifically targeting apoptotic cells, and completed the present invention.

Accordingly, an object of the present invention is to provide a peptide specifically targeting apoptotic cells and a use thereof.

To attain the object, in an aspect, the present invention provides an isolated polypeptide consisting of the sequence (I):

Cys-X1-Val-Ala-Pro-X2             (I)

wherein X1 is an amino acid with polar uncharged side chain and X2 is an amino acid with positive charged side chain In another aspect, the present invention provides a polynucleotide encoding the peptide.

In another aspect, the present invention provides a vector comprising the polynucleotide.

In another aspect, the present invention provides a transfectant transformed with the vector.

In another aspect, the present invention provides a composition for detecting of apoptotic cells comprising the polypeptide as an effective ingredient.

In another aspect, the present invention provides a method for detecting apoptotic cells comprising the steps of: (a) mixing the polypeptide with a sample; (b) removing unbound or unspecifically bound polypeptide; and (c) detecting the binding and the location of the polypeptide.

In another aspect, the present invention provides a composition for drug delivery comprising the polypeptide as an effective ingredient.

In another aspect, the present invention provides a pharmaceutical composition for preventing and treating neoplastic disease comprising the polypeptide and an antitumor agent bound thereto as effective ingredients.

In another aspect, the present invention provides a composition for imaging neoplastic disease site comprising the polypeptide as an effective ingredient.

In another aspect, the present invention provides a pharmaceutical composition for preventing and treating stroke comprising the polypeptide and a anti-strok agent bound thereto as effective ingredients.

In another aspect, the present invention provides a composition for imaging stroke site comprising the polypeptide as an effective ingredient.

In another aspect, the present invention provides a pharmaceutical composition for treating myocardial infarction comprising the polypeptide and an anti-myocardial infection agent bound thereto as effective ingredients.

In another aspect, the present invention provides a composition for imaging myocardial infarction site comprising the polypeptide as an effective ingredient.

In another aspect, the present invention provides a pharmaceutical composition for preventing and treating arteriosclerosis comprising the polypeptide and an anti-arteriosclerosis agent bound thereto as effective ingredients.

In another aspect, the present invention provides a composition for imaging arteriosclerosis site comprising the polypeptide as an effective ingredient.

In another aspect, the present invention provides a method for drug delivery comprising administering the polypeptide and a drug bound thereto to a subject in need thereof at an effective dose.

In another aspect, the present invention provides a method for treating neoplastic disease comprising administering the polypeptide and an antitumor agent bound thereto to a subject in need thereof at an effective dose.

In another aspect, the present invention provides a method for treating stroke comprising administering the polypeptide and an antistroke agent bound thereto to a subject in need thereof at an effective dose.

In another aspect, the present invention provides a method for treating myocardial infarction comprising administering the polypeptide and an anti-myocardial infarction agent bound thereto to a subject in need thereof at an effective dose.

In another aspect, the present invention provides a method for treating arteriosclerosis comprising administering the polypeptide and an anti-arteriosclerosis agent bound thereto to a subject in need thereof at an effective dose.

In another aspect, the present invention provides a method for imaging a disease site selected from a group consisting of neoplastic disease, stroke, myocardial infarction and arteriosclerosis comprising administering the peptide to a subject in need thereof at an effective dose.

BRIEF DESCRIPTION OF THE DRAWINGS

FIG. 16 shows the images obtained as follows. A nude mouse to which a tumor was xenotransplanted was injected with the polypeptide of the present invention (ApoPep-2) that was labeled with fluorescence, and then the peptide was traced in vivo based on fluorescence (A). A nude mouse to which a tumor was xenotransplanted was treated with (Dox+) or without doxorubicin (Dox−). 12 hours later, ApoPep-2 or control peptide, which was labeled with fluorescence, was injected into blood and was traced in vivo based on fluorescence (B). Tumor and other organs were isolated and observed ex vivo for fluorescence (C).

DETAILED DESCRIPTION

Figure 1:
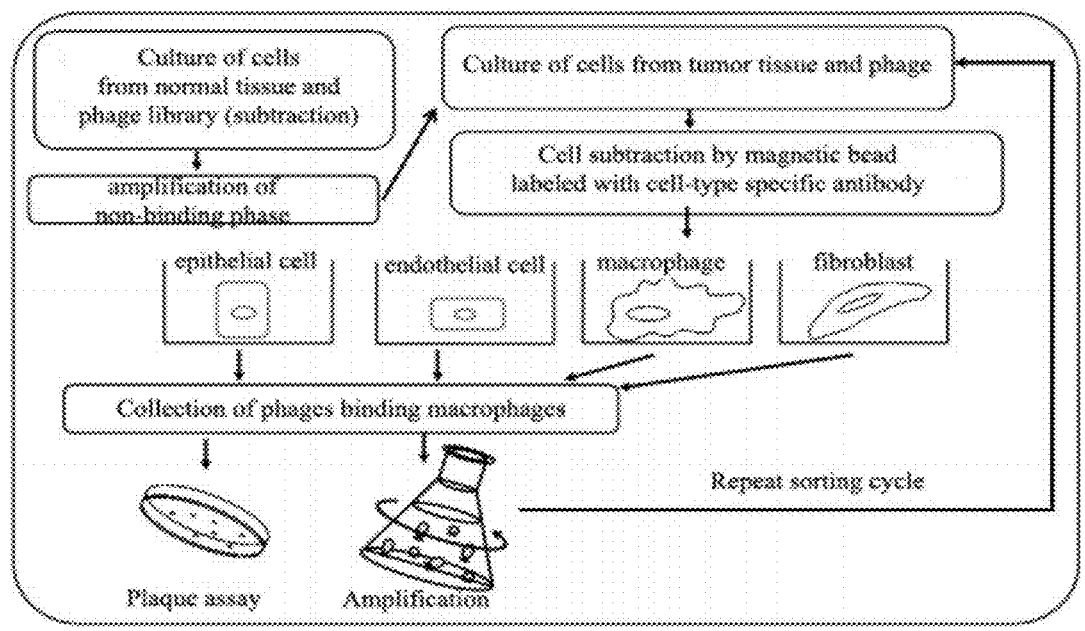
FIG. 1 schematically illustrates a process of screening phages specifically binding to various cells (tumor cells, endothelial cells, macrophages and fibroblasts) derived from human primary lung cancer tissue.

Hereinafter, the present invention will be described in further detail.

Based on the finding that a polypeptide having an amino acid sequence represented by anyone selected from the group consisting of SEQ ID NO: 1 to SEQ ID NO: 12 specifically binds to apoptotic cells undergoing apoptosis, the present invention provides a polypeptide with a novel sequence having an amino acid sequence represented by anyone selected from the group consisting of SEQ ID NO: 1 to SEQ ID NO: 12, a composition for detection of apoptotic cells comprising the polypeptide and so on, as a use thereof.

Based on the finding that a polypeptide consisting of the sequence (I):

Cys-X1-Val-Ala-Pro-X2        (I)

wherein X1 is an amino acid with polar uncharged side chain and X2 is an amino acid with positive charged side chain, specifically binds to apoptotic cells undergoing apoptosis, the present invention provides an isolated polypeptide consisting of the sequence (I):

Cys-X1-Val-Ala-Pro-X2        (I)

wherein X1 is an amino acid with polar uncharged side chain and X2 is an amino acid with positive charged side chain, a composition for detection of apoptotic cells comprising the polypeptide and so on, as a use thereof.

The peptide of the present invention is a peptide which specifically binds to apoptotic cells undergoing apoptosis and has an amino acid sequence represented by anyone selected from the group consisting of SEQ ID NO: 1 to SEQ ID NO: 12.

The isolated polypeptide of the present invention is a polypeptide which specifically binds to apoptotic cells undergoing apoptosis and consisting of the sequence (I):

Cys-X1-Val-Ala-Pro-X2        (I)

wherein X1 is an amino acid with polar uncharged side chain and X2 is an amino acid with positive charged side chain.

Preferably, the said amino acid with polar uncharged side chain is Ser or Thr, and/or the said amino acid with positive charged side chain is Arg or Lys.

More preferably, the isolated polypeptide is selected from the group consisting of SEQ ID NO: 2 and SEQ ID NOs: 10 to 12.

As used herein, a peptide fragment refers to any peptide, protein, mimetic peptide, compound and biological agent capable of specifically binding to apoptotic cells. The peptide of the present invention may be derived from the nature or may be synthesized by a known peptide synthesis technique.

The peptide of the present invention may comprise the peptide having naturally occurring amino acid sequences and variants having modified sequences as well. The variants of the peptide of the present invention refer to peptides having different sequences from the amino acid sequence selected from the group consisting of SEQ ID NO:1 to SEQ ID NO:12, prepared by deletion, insertion, non-conserved or conserved substitution, substitution of amino acid analog or their combinations. The silent alteration of amino acid residues not to substantially impair protein activity is well known to one skilled in the art (H. Neurath, R. L. Hill, The Proteins, Academic Press, New York, 1979).

In addition, the peptide of the present invention may comprise modifications such as phosphorylation, sulfation, acrylation, glycosylation, methylation, farnesylation and the like.

Further, the present invention provides a polynucleotide having a base sequence encoding the peptide of the present invention. The polynucleotide may be any combination of base sequences, which, consequently, is capable of encoding the peptide of the present invention.

In addition, the present invention provides a vector having a base sequence encoding the peptide of the present invention and a transformant transformed by the vector.

The vectors of the present invention include a plasmid vector, a cosmid vector, a bacteriophage vector and a viral vector, but are not limited thereto. The vectors of the present invention may conventional cloning vectors or expression vectors, and the expression vectors comprise regulatory elements for gene expression such as a promoter, operator, an initiation codon, a stop codon, a polyadenylation signal, and an enhancer (promoting gene), and a variety of vectors can be prepared according to the purpose. Furthermore, the said vectors may comprise selective markers for selecting host cells comprising the vector and in case of replicable vectors, they comprise replication origin.

The transformation with the said vector can be carried out according to any known transformation method in the pertinent art. Preferably, microprojectile bombardment, electroporation, $CaPO_4$ precipitation, $CaCl_2$ precipitation, PEG-mediated fusion, microinjection and liposome-mediated method, but not limited to. The transformant may be *Escherichia coli, Bacillus subtilis, Streptomyces, Pseudomonas, Proteus mirabilis* and *Staphylococcus, Agrobacterium tumefaciens*, but not limited to.

Through various experiments aimed at verifying the functions of peptides identified to specifically bind to apoptotic cells, the inventors of the present invention have confirmed that the peptide of the present invention specifically recognizes cultured tumor cells, normal epithelial cells and macrophages undergoing apoptosis and binds to the cells. Further, we have verified that the peptides of the present invention are capable of targeting apoptotic cells in a tumor tissue and, thereby, enabling in vivo imaging and monitoring thereof. Accordingly, it was confirmed that the peptide of the present invention may be utilized for a composition for detection of apoptotic cells, for a composition for diagnosis or monitoring of apoptosis in tumor tissue, and for a pharmaceutical composition for prevention and treatment of neoplastic disease along with an antitumor agent.

More specifically, in an example of the present invention, phages specifically binding to macrophages or endothelial cells separated from a tumor tissue were screened using a commercially available T7 phage library. Through a total of 3 rounds of screening, phages capable of specifically binding to the cells were screened. Through sequencing, it was confirmed that peptides having the amino acid sequence CQRPPR (SEQ ID NO: 1), CSVAPR (SEQ ID NO: 2), CNRPPR (SEQ ID NO: 3), CQKPPR (SEQ ID NO: 4), CQRPPK (SEQ ID NO: 5), CNKPPR (SEQ ID NO: 6), CNRPPK (SEQ ID NO: 7), CQKPPK (SEQ ID NO: 8), CNKPPK (SEQ ID NO: 9), CTVAPR (SEQ ID NO: 10), CSVAPK (SEQ ID NO: 11) and CTVAPK (SEQ ID NO: 12) were mainly screened out. It seems that the peptides of the present invention are synthesized by the nucleotides inserted with termination codon after 5th amino acid in the phage library of the present invention randomly encoding $CX_7C$ peptide.

In another example of the present invention, it was investigated whether the peptide of the present invention targets a tumor xenotransplanted under the skin of nude mouse and which cell it binds to. As a result, the peptides of the present invention were confirmed, when injected into blood, to target the tumor tissue and mainly bind to the tumor cells undergoing apoptosis rather than macrophages or endothelial cells, from tissue staining.

In another example of the present invention, the binding specificity of the screened peptides to the apoptotic cells induced by chemical was investigated. As a result, the peptide strongly bound to the apoptotic cells treated with an apoptosis-inducing agent, whereas it hardly bound to the untreated cells. Further, the binding of the peptide to the apoptotic cells was not inhibited by the prior treatment of annexin V at high concentration. In addition, the peptide was confirmed to recognize and bind to the cells in the later stage of apoptosis as well as the early stage.

In another example of the present invention, it was investigated whether the peptide of the present invention targets a tumor xenotransplanted under the skin of nude mouse and whether it can be imaged. As a result, the peptide of the present invention targeted the tumor tissue in the group to which the peptide of the present invention was injected into blood following doxorubicin treatment and the targeting could be imaged by fluorescent label. In contrast, the targeting was not observed in the group to which the peptide of the present invention was injected without the drug treatment as well as in the group to which a control peptide was injected following the drug treatment.

In another example of the present invention, it was investigated whether the peptide of the present invention labeled with a radioactive isotope targets a tumor xenotransplanted under the skin of nude mouse and whether it can be imaged by positron emission tomography (PET). As a result, the targeting of the peptide of the present invention was confirmed in the group to which the peptide of the present invention labeled with $^{123}I$ (I-123) was injected into blood following doxorubicin treatment, through increased PET image signals at the tumor site. In contrast, in the group to which $^{18}F$ (F-18)-labeled fluorodeoxyglucose (FDG), which is frequently used for PET, was injected, the PET image signals decreased at the tumor site following the drug treatment.

In another example of the present invention, it was investigated whether the peptide of the present invention targets in the aorta of an arteriosclerosis-induced mouse and whether it can be imaged. As a result, the peptide of the present invention targeted in the aorta of arteriosclerotic mice in the group to which the peptide of the present invention was injected into blood, and the targeting could be imaged using a fluorescent label. In contrast, the targeting of the peptide could not be observed in the group of arteriosclerotic mice to which a control peptide was injected or in the group of normal mice.

In another example of the present invention, it was investigated whether the peptide of the present invention targets in the brain tissue of a stroke-induced rat and whether it can be imaged. As a result, the peptide of the present invention targeted in the damaged brain tissue of the group of stroke-induced rats to which the peptide of the present invention was injected into blood, and the targeting could be imaged using a fluorescent label. In contrast, the targeting of the peptide could not be observed in the group of stroke-induced rats to which a control peptide was injected or in the group of normal rats.

In another example of the present invention, it was investigated whether the peptide of the present invention targets in the cardiac tissue of a myocardial infarction-induced rat and whether it can be imaged. As a result, the peptide of the present invention targeted in the damaged cardiac tissue of the group of myocardial ischemia-induced rats to which the peptide of the present invention was injected into blood, and the targeting could be imaged using a fluorescent label. In contrast, the targeting of the peptide could not be observed in the group of myocardial ischemia-induced rats to which a control peptide was injected or in the group of normal rats.

In another example of the present invention, it was investigated whether the polypeptide of the present invention targets a tumor xenotransplanted under the skin of nude mouse and which cell it binds to. As a result, the polypeptides of the present invention (ApoPep-2) were confirmed, when injected into blood, to target the tumor tissue and mainly bind to the tumor cells undergoing apoptosis.

In another example of the present invention, the binding specificity and strength of the polypeptide of the present invention (ApoPep-2) to the apoptotic cells induced by chemical was investigated. Apoptosis-inducing agent treated cells were reacted with the polypeptide of the present invention (ApoPep-2). The binding properties of the polypeptide of the present invention (ApoPep-2) to apoptotic cells, competitive inhibition by annexin V was measured. Necrosis-induced cells were reacted with the polypeptide of the present invention (ApoPep-2). As a result, the polypeptide of the present invention (ApoPep-2) strongly bound to the apoptotic cells treated with an apoptosis-inducing agent (etoposide or trail), whereas it hardly bound to the untreated cells. Further, the binding of the polypeptide of the present invention (ApoPep-2) was not inhibited by the treatment with annexin V at high concentration. Further, the polypeptide of the present invention did not bind to the necrosis-induced cells.

In another example of the present invention, it was investigated whether the polypeptide of the present invention (ApoPep-2) targets a tumor xenotransplanted under the skin of nude mouse and whether it can be imaged.

As a result, the polypeptide of the present invention (ApoPep-2) targeted the tumor tissue in the group to which the polypeptide of the present invention was injected into blood following doxorubicin treatment and the targeting could be imaged by fluorescent label. In contrast, the targeting was not observed in the group to which the polypeptide of the present invention was injected without the drug treatment as well as in the group to which a control peptide was injected following the drug treatment. Further, the fluorescence signals from the kidney of all the groups were strong due to the renal clearance of peptides.

To conclude, it was confirmed that the peptide of the present invention binds specifically to apoptotic cells, thereby recognizing apoptosis and targeting tumors in vivo.

The following references may be referred to the processes for the said nucleotides and proteins (Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990)).

Accordingly, the present invention provides an composition for detecting apoptotic cells comprising an peptide having an amino acid sequences represented by anyone selected from the group consisting of SEQ ID NO: 1 to SEQ ID NO: 12 of the present invention as an effective ingredient.

Accordingly, the present invention provides an composition for detecting apoptotic cells comprising an polypeptide of the present invention as an effective ingredient, consisting of the sequence (I): Cys-X1-Val-Ala-Pro-X2 (I), wherein X1 is an amino acid with polar uncharged side chain and X2 is an amino acid with positive charged side chain.

For easy identification, detection and qualification of binding the peptide of the present invention with apoptotic cell, the peptide of the present invention may be provided as a form of labeled. The said detectable label material may be coloring enzyme (for example, peroxidase, alkaline phosphatase), radioactive isotope (for example, $^{18}F$, $^{124}I$, $^{125}I$, $^{32}P$, $^{35}S$), chromophore, scintillating materials or fluorescent materials (for example: FITC, RITC, fluorescent proteins (GFP (Green Fluorescent Protein); EGFP (Enhanced Green Fluorescent Protein), RFP (Red Fluorescent Protein); DsRed (*Discosoma* sp. red fluorescent protein); CFP (Cyan Fluorescent Protein), CGFP (Cyan Green Fluorescent Protein), YFP (Yellow Fluorescent Protein), Cy3, Cy5 and Cy7.5), super paramagnetic particles or ultrasuper paramagnetic particles.

Detection techniques based on labeling are well known in the art. Detections may be made, for example, as follows. In case a fluorescent material is used as a detectable label, immunofluorescence staining may be employed. For example, the peptide of the present invention labeled with a fluorescent material may be reacted with a sample, and, following the removal of unbound or unspecifically bound product, fluorescence emitted by the peptide may be observed under a fluorescence microscope. In case that an enzyme is used as a detectable label, absorbance may be measured following an enzymatic reaction with a substrate. And, in case that a radioactive material is used, a radioactive radiation may be measured. The detection result may be imaged using a known imaging technique.

The present invention further provides a method for detecting apoptotic cells comprising the steps of: (a) mixing the polypeptide of the present invention with a sample; (b) removing unbound or unspecifically bound polypeptide; and (c) detecting the binding of the polypeptide and the location thereof. The polypeptide of the present invention and the detection of the polypeptide of the present invention bound to apoptotic cells may be described above or carried out as described above or according to known methods.

Further, the present invention provides a use of the polypeptide of the present invention for detection of apoptotic cells. The polypeptide of the present invention and the detection of the polypeptide of the present invention bound to apoptotic cells may be described above or carried out as described above or according to known methods.

Since the peptide of the present invention is capable of specifically binding to apoptotic cells, it may be utilized as an intelligent drug carrier which selectively delivers a drug to the cells. Accordingly, the present invention provides a composition for drug delivery comprising the peptide of the present invention as an effective ingredient. Further, the present invention provides a use of the peptide of the present invention for drug delivery. In addition, the present invention provides a method for drug delivery comprising administering the peptide of the present invention and a drug bound thereto to a subject in need thereof at an effective dose.

As described above, apoptosis occurs not only in tumor cells, but also in the cells affected by stroke, myocardial infarction or arteriosclerosis (Thomson, *Science*, 1995, 67:1456-1462; Du et al, *J. Cereb. Blood Flow Metab.*, 1996, 16:195-201; Narula et al., *New Engl. J. Med.*, 1996, 335: 1182-1189). Accordingly, the composition for drug delivery may be specific to neoplastic disease, stroke, myocardial infarction or arteriosclerosis. As used herein, the neoplastic disease is a disease exhibiting pathological conditions due to malignant tumors. Examples of neoplastic disease may include, although not limited thereto, colon cancer, lung cancer, stomach cancer, esophageal cancer, pancreatic cancer, gallbladder cancer, renal cancer, bladder cancer, prostate cancer, testicular cancer, cervical cancer, endometrial cancer, choriocarcinoma, ovarian cancer, breast cancer, thyroid cancer, brain cancer, head and neck cancer, malignant melanoma, skin cancer, liver cancer, leukemia, lymphoma, multiple myeloma, chronic myelogenous leukemia, neuroblastoma and aplastic anemia.

When used in combination with existing antitumor agent, anti-myocardial infarction agent, antistroke agent or anti-arteriosclerosis agent, the peptide of the present invention may selectively deliver the agents to the disease site, i.e., tumor site, myocardial infarction site, stroke site or arteriosclerosis site. Hence, the drug efficiency may be improved and side effects on normal tissues may be significantly reduced.

The antitumor agent that can be used in combination with the peptide of the present invention may be anyone that is used for treatment of a tumor. For example, paclitaxel, doxorubicin, vincristine, daunorubicin, vinblastine, actinomycin-D, docetaxel, etoposide, teniposide, bisantrene, homoharringtonine, Gleevec (STI-571), cisplatin, 5-fluorouracil, adriamycin, methotrexate, busulfan, chlorambucil, cyclophosphamide, melphalan, nitrogen mustard, nitrosourea, etc. may be included. And, the anti-myocardial infarction agent, antistroke agent and anti-arteriosclerosis agent may be anyone used for the treatment of the diseases. For example, thrombolytic drugs such as streptokinase, urokinase, alteplase, etc, which are used for removal of thrombis blocked blood vessel in stroke and myocardial infarction, may be used. Further, myocardial cell protecting agents such as angiotensin II inhibitor, aldosterone receptor inhibitor, erythropoietin, etc. may be used. Also, brain nerve cell protecting agents such as N-methyl-D-aspartate (NMDA) receptor inhibitor may be used. Further, cholesterol synthesis inhibiting or blood cholesterol level reducing drugs such as lovastatin, vascular smooth muscle cell (VSMC) proliferating inhibiting drugs such as rapamycin, antiinflammatory drugs such as Celebrex, platelet coagulation inhibiting drugs such as Ticlopin, matrix metalloproteinase inhibiting drugs such as marimastat, Trocade, etc. may be used. The binding of the peptide of the present invention with the agents may be carried out by the methods known in the art, for example, by covalent bonding, crosslinking, or the like. For this, the peptide of the present invention may be chemically modified insofar as its activity is not lost, if necessary. The amount of the peptide of the present invention included in the composition of the present invention may be different depending on the kind and amount of the anticancer drug that the peptide binds to.

As used herein, the "effective amount" refers to the amount effective in treating the subject diseases, and the "subject" refers to mammals, particularly, animals comprising human. The subject may be human in need of treatment.

Meanwhile, the present invention provides a pharmaceutical composition for prevention and treatment of neoplastic disease comprising the peptide of the present invention and an antitumor agent bound thereto as effective ingredients. In addition, the present invention provides a use of the peptide of the present invention and an antitumor agent bound thereto for the preparation of an agent treating neoplastic disease. Furthermore, the present invention provides a method for treatment of neoplastic disease comprising administering the peptide of the present invention and an antitumor agent bound thereto to a subject in need thereof at an effective dose.

At this time, in the said pharmaceutical composition, antitumor agent, binding method and neoplastic disease are the same as can be seen from the foregoing Meanwhile, a pharmaceutical composition of the present invention may be prepared by formulated into pure form or appropriate forms with pharmaceutically acceptable carriers. As used herein, the term "pharmaceutically acceptable" means nontoxic composition which is physiologically acceptable and, when administered to human beings, generally does not cause allergic reactions, such as gastrointestinal disorder and dizziness, or similar reactions thereto. The said carriers may comprise all kinds of solvents, dispersing medium, water-in-oil or oil-in-water emulsion, aquatic composition, liposome, microbead and microsome, biodegradable nanoparticles.

Meanwhile, the pharmaceutical composition of the present invention may be formulated with appropriate carriers according to administration routes. The pharmaceutical composition of the present may be administered orally or parenterally, but not limited thereto. The parenteral administration routes may comprise route by intracutaneous, intranasal, intraperitoneal, intramuscular, subdural, or intravenous and the like.

For oral administration, which is not limited thereto, the composition of the present invention can be formulated in the form of powder, granule, tablets, pills, sugar-coated tablets, capsules liquor, gel, syrup, suspension, wafer and the like. The appropriate carriers may comprise sugars comprising lactose, dextrose, sucrose, sorbitol, mannitol, xylitol, erythritol and maltitol, starches comprising corn starch, wheat starch, rice starch and potato starch, celluloses comprising cellulose, methylcellulose, sodium carboxymethylcellulose, and hydroxypropylmethyl-cellulose, and fillers such as gelatin and polyvinylpyrrolidone. In addition, it may comprise crosslinked polyvinylpyrrolidone, agar, alginic acid or a sodium salt thereof as a solutionizer. Furthermore, the said pharmaceutical composition may further comprise antiagglutination reagent, lubricant, humectant, flavor, emulsifying agent and antiseptic.

In addition, in case of parenteral administration, the pharmaceutical composition of the present invention could be formulated, as known in the art, in the form of injectable formulation, transdermal formulation and intranasal formulation with proper parenteral carriers. The injectable formulation must be sterilized and prevented from contamination of microorganisms such as fungi and bacteria. In case of injectable formulation, the carriers may comprise, but not limited to, water, ethanol, polyol (for example, glycerol, propylene glycol, liquid polyethylene glycol and the like), mixture of these and/or solvent including vegetable oils or dispersion medium. More preferably, the carriers may comprise Hank's solution, Ringer's solution, PBS (phosphate buffered saline) containing triethanolamine, or isotonic solutions such as water for injection, 10% ethanol, 40% propylene glycol, and 5% dextrose. To prevent from contamination of microorganisms, the injectable agents may comprise additionally antifungal reagents and anti-bacterial reagents such as parabens, chlorobutanol, phenol, sorbic acid, thimerosal. In addition, the injectable formulation may also comprise isotonic solution such as saccharides or sodium chloride in mose cases. These formulations are described in *Remington's Pharmaceutical Science,* 15th Edition, 1975, Mack Publishing Company, Easton, Pa. which is well know prescription manual.

In case of intranasal preparations, the inventive pharmaceutical composition may comprise proper propellant such as dichlorofluoromethane, trichlorofluoromethane, dichlorotetafluoroethane, carbon dioxide, and the like. By these propellants, the composition could be released easily from pressurized pack or spray container in the form aerosol spray. In case of the pressurized aerosol, administration dosage may be set by placing a valve. For example, gelatin capsules and cartridges which are used in inhalers and insufflators may comprise a proper powder mixture such as a chemical compound, lactose, or starches Another carriers which is pharmaceutically acceptable is disclosed in Remington's Pharmaceutical Sciences, 19th ed. Mack Publishing Company, Easton, Pa., 1995.

The inventive pharmaceutical composition may further comprise one or more buffers (for example, saline or PBS), carbohydrates (for example, glucose, mannose, sucrose, or dextran), antioxidants, bacteriostats, chelating reagents (for example, EDTA or glutathione), adjuvant (for example, aluminium hydroxide), suspension reagent, concentrating reagent, and/or preservatives.

Also, the inventive pharmaceutical composition may be formulated by using the method which is known in the art, to provide rapid, continuous or delayed release after administered to a mammalian.

The pharmaceutical composition formulated by the said method may be administered by oral, transdermal, subcutaneous, intramuscular, or intravenous with effective amount. The said "effective amount" means the amount of compound or extract which makes traceable for diagnosis or treatment, when it is administered to a patient. The administration amount of the pharmaceutical composition of the present invention may be suitably determined by considering administration route, administration subject, the subject disease and severity thereof, age, sex, body weight, variation of the individuals, and health condition. The pharmaceutical composition of the present invention containing the inventive polypeptide may vary depending on the severity of the disease, but the effective ingredient may be generally administered at an effective dose of 10 µg-10 mg several times daily.

Further, since the peptide of the present invention specifically binds to apoptotic cells, it may be useful for imaging and diagnosis of neoplastic disease site. Accordingly, the present invention provides a composition for imaging and diagnosis of neoplastic disease comprising the peptide as an effective ingredient. The present invention further provides a use of the peptide of the present invention for imaging neoplastic disease site. In addition, the present invention provides a method for imaging neoplastic disease site comprising administrating the peptide of the present invention to a subject in need thereof at an effective dose. The imaging and diagnosis of neoplastic disease may be for the purpose of not only early diagnosis of neoplastic disease but also monitoring of disease progression, therapeutic effect of tumor treatment and response to the treatment, without being limited thereto. The peptide may be labeled for easier identification, detection and quantitation of binding, as described above.

Further, since the peptide of the present invention specifically binds to apoptotic cells, the peptide of the present invention may deliver a drug to apoptotic cells at stroke, myocardial infarction and arteriosclerosis sites, not only at tumor sites. Thus, the present invention provides a pharmaceutical composition for prevention and treatment of stroke comprising the peptide of the present invention and an antistroke agent bound thereto as effective ingredients. Further, the present invention provides a pharmaceutical composition for prevention and treatment of myocardial infarction comprising the peptide of the present invention and an anti-myocardial infarction agent bound thereto as effective ingredients. In addition, the present invention provides a pharmaceutical composition for prevention and treatment of arteriosclerosis comprising the peptide of the present invention and an anti-arteriosclerosis agent bound thereto as effective ingredients.

In addition, the present invention provides a use of the peptide and an antistroke agent bound thereto for the preparation of an agent treating stroke. The present invention provides a method for treating stroke comprising administering the peptide and an antistroke agent bound thereto to a subject in need thereof at an effective dose.

Meanwhile, the present invention provides a use of the peptide and an anti-myocardial infarction agent bound thereto for the preparation of an agent treating myocardial infarction. The present invention provides a method for treating myocardial infarction comprising administering the peptide of the present invention and an anti-myocardial infarction agent bound thereto to a subject in need thereof at an effective dose.

Meanwhile, the present invention provides a use of the peptide of the present invention and an anti-arteriosclerosis agent bound thereto for the preparation of an agent treating arteriosclerosis. The present invention provides a method for treating of arteriosclerosis comprising administering the peptide of the present invention and an anti-arteriosclerosis agent bound thereto to a subject in need thereof at an effective dose.

When used in combination with existing antistroke agent, anti-myocardial infarction agent or anti-arteriosclerosis agent, the peptide of the present invention may selectively deliver the agents to the disease site. Hence, the drug efficiency may be improved and side effects on normal tissues may be significantly reduced.

The anti-myocardial infarction agent, antistroke agent and anti-arteriosclerosis agent agent of the present invention that can be used in combination with the peptide of the present invention may be anyone that is used for treatment thereof, and for example, streptokinase, urokinase, alteplase, angiotensin II inhibitor, aldosterone receptor inhibitor, erythropoietin, NMDA (N-methyl-D-aspartate) receptor inhibitor, Lovastatin, Rapamycin, Celebrex, Ticlopin, Marimastat, Trocade, and etc. may be used. The binding of the peptide of the present invention with the agents may be carried out by the methods known in the art, for example, by covalent bonding, crosslinking, or the like. For this, the peptide of the present invention may be chemically modified insofar as its activity is not lost, if necessary. The amount of the peptide of the present invention included in the composition of the present invention may be different depending on the kind and amount of the agent that the peptide binds to.

Further, since the peptide of the present invention specifically binds to apoptotic cells, it may be useful for imaging and diagnosis of the site of stroke, myocardial infarction and arteriosclerosis. Accordingly, the present invention provides a composition for imaging the site of stroke comprising the peptide of the present invention as an effective ingredient. In addition, the present invention provides a composition for imaging the site of myocardial infarction comprising the peptide as an effective ingredient. Further, the present invention provides a composition for imaging the site of arteriosclerosis comprising the peptide as an effective ingredient.

Meanwhile, the present invention provides a use the peptide of the present invention for imaging a disease site selected from a group consisting of neoplastic disease, stroke, myocardial infarction and arteriosclerosis. The present invention provides a method for imaging a disease site selected from a group consisting of neoplastic disease, stroke, myocardial infarction and arteriosclerosis comprising administering the peptide to a subject in need thereof at an effective dose.

The imaging and diagnosis of disease may be for the purpose of not only early diagnosis of disease but also monitoring of disease progression, therapeutic effect of treatment and response to the treatment, without being limited thereto. The peptide may be labeled for easier identification, detection and quantitation of binding, as described above.

As described, the peptide of the present invention having an amino acid sequence represented by anyone selected from the group consisting of SEQ ID NO: 1 to SEQ ID NO: 12 is capable of specifically binding to apoptotic cells.

As described, the polypeptide of the present invention consisting of the sequence (I): Cys-X1-Val-Ala-Pro-X2 (I), wherein X1 is an amino acid with polar uncharged side chain and X2 is an amino acid with positive charged side chain, is capable of specifically binding to apoptotic cells. Accordingly, the peptide of the present invention may be useful for detection of apoptotic cells, as well as detection and imaging of apoptotic cells in tumor tissue, apoptotic myocardial cells in myocardial infarction tissue, apoptotic nerve cells in stroke tissue and arteriosclerosis site, and targeted drug delivery thereto.

EXAMPLES

The examples and experiments will now be described. The following examples and experiments are for illustrative purposes only and not intended to limit the scope of this disclosure.

Example 1

Screening of Peptide Having Binding Specificity to the Cells of Tumor Tissue <1-1> Preparation of Phage Peptide Library In order to find out peptides specific to various cells constituting a tumor tissue, the inventors of the present invention employed the phage peptide display technique (Smith, *Science*, 228:1315-1317, 1985). Phage peptide display refers to displaying peptides composed of several to dozens of amino acids on the surface of bacteriophage. Since a phage library with as many as $10^9$ peptides can be prepared, the technique is useful in screening a large number of peptides at once and finding out the peptides targeting desired tissue or tumor.

The phage peptide library used in the present invention was prepared as follows. Oligonucleotides coding for CX7C peptides having cysteine at both ends and 7 random amino acids between them were randomly synthesized. The oligonucleotide synthesis was carried out by Macrogen (Korea). Then, the synthesized oligonucleotides were cloned into the capsid protein gene constituting 1 the surface of T7 415-1b phage using a T7SELECT® phage cloning kit of Novagen (USA), according to the manufacturer's instructions, thereby preparing phage peptide library. The diversity of the prepared phage peptide library was measured at about 5×108 pfu.

<1-2> Screening of Phage Peptide Library

Tumor tissues and normal tissues neighboring the tumors, which had been obtained from surgical operations for tumor treatment, were finely cut using a knife, and grinded using a tissue homogenizer to prepare a cell suspension. The phage library prepared in Example <1-1> was mixed with the cell suspension obtained from the normal tissue, and they were allowed to react at 4° C. for 2 hours. After completion of the reaction, only the supernatant was taken. After recovering the phages not bound to normal cells, and the titer was amplified using BL21 *E. coli* as host. Subsequently, the cell suspension obtained from the tumor tissue was reacted under the same condition. The phages weakly binding to tumor cells unspecifically were removed by washing with 1 mL of DMEM (Dulbecco's modified Eagle's medium) containing 1% bovine serum albumin (BSA) for 5 minutes at room temperature, for a total of 3 times. Following the washing, magnetic beads on which anti-macrophage antibody (anti-CD14 antibody, Dynal) or anti-endothelial cell antibody (anti-CD31 antibody, Dynal) was attached was reacted with the cell suspension at 4° C. for 30 minutes. Then, the cells adhering to the respective magnetic beads were isolated. The isolated macrophages or endothelial cells were treated with 100 μL of DMEM containing 1% NP-40 at 4° C. for 10 minutes. Then, after adding 900 μL of BL21 *E. coli* culture medium, the phages binding to the cells were detected. The titer was measured for part of the detected phages according to a method known in the art (Phage display, Clackson T and Lowman H B, p. 171, 2004, Oxford University Press, New York). The remaining phages were amplified. This procedure was repeated for a total of 3 times. As a result, the titer of the phages binding to the macrophages and endothelial cells derived from the tumor tissue increased remarkably, therby considering that the screening was successfully performed. The above procedure is schematically shown in FIG. 1.

<1-3> Nucleotide Sequencing and Amino Acid Sequencing of Phage Clone

In order to investigate which peptide was displayed for the phages screened in Example <1-2>, 30 phage clones were randomly selected for each cell, and the nucleotides inserted in the phages were amplified by PCR and sequenced. The 5'-primer was the oligonucleotide AGCGGACCAGAT-TATCGCTA (SEQ ID NO: 13) and the 3'-primer was the oligonucleotide AACCCCTCAAGACCCGTTTA (SEQ ID NO: 14). PCR was carried out with pre-denaturation of template DNA for 5 minutes at 95° C.; 35 cycles of 50 seconds at 94° C., 1 minute at 50° C., and 1 minute at 72° C.; and final extention for 6 minutes at 72° C.

The PCR product was sequenced by DNA sequencing company, Bioneer. Based on the resultant nucleotide sequence, the amino acid sequence was deduced. Through analysis of the deduced amino acid sequence using the ClustalW program, the peptides of the representative phage clones most frequently occurring for the macrophages and endothelial cells were obtained, respectively. They represented SEQ ID NO: 1 (ApoPep-1, CQRPPR, screened for the macrophages), SEQ ID NO: 2 (ApoPep-2, CSVAPR, screened for the endothelial cells), SEQ ID NO: 3 (CNRPPR), SEQ ID NO: 4 (CQKPPR), SEQ ID NO: 5 (CQRPPK), SEQ ID NO: 6 (CNKPPR), SEQ ID NO: 7 (CNRPPK), SEQ ID NO: 8 (CQKPPK), SEQ ID NO: 9 (CNKPPK), SEQ ID NO: 10 (CTVAPR), SEQ ID NO: 11 (CSVAPK) and SEQ ID NO: 12 (CTVAPK)

Example 2

Histological Evaluation of In Vivo Tumor Targeting by the Peptide of the Present Invention <2-1> Preparation of Tumor Xenotransplantation Model of Nude Mouse All animal experiments were performed in accordance with the guideline of the Institutional Animal Care and Use Committee. For tumor xenotransplantation, human lung cancer cells (A549, 1×10$^7$ cells) suspended in RMPI-1640 medium was subcutaneously injected at the right upper or lower limb of a 6-week-old male BALB/c nude mouse (Hyochang Science). Then, 3 weeks were given for the tumor to grow to a size of 0.5 to 1 cm. The A549 cell line used in the experiment was cultured in RMPI-1640 medium containing 10% fetal bovine serum (FBS) in which antibiotics (penicillin and streptomycin) were included. Subculturing was performed every 3 or 4 days.

<2-2> Histological Analysis of Tumor Targeting

The peptides used in the present invention were fluorescein-attached form at the N-terminal. They were synthesized according to the standard Fmoc technique and then isolated through HPLC. The peptide synthesis was performed by an expertise company (Peptron).

The peptide of the present invention (ApoPep-1) or a control peptide (amino acid sequence: NSSSVDK), labeled with fluorescein, was injected into the tail vein of a mouse under isoflurane anesthesia, to a final concentration of 50 μM, and 2 hours was given for circulation.

For histological analysis, the mouse was anesthetized and the abdomen was cut open. After sequentially perfusing phosphate-buffered saline (PBS) and 4% paraformaldehyde through the heart, tumor tissues and organs were removed. Each tissue was cryosected and the peptide of the present invention was observed under a fluorescence microscope (Zeiss). Apoptosis in the tumor tissue was confirmed by TUNEL (in vitro terminal deoxynucleotidyl transferase-mediated dUTP nick-end labeling) assay according to the instructions of the manufacturer (Chemicon). Fibrinogen staining was performed by immunohistochemistry using anti-fibrinogen antibody (Abcam) and secondary antibody labeled with Alexa 568, a red fluorescent reagent.

Figure 2:
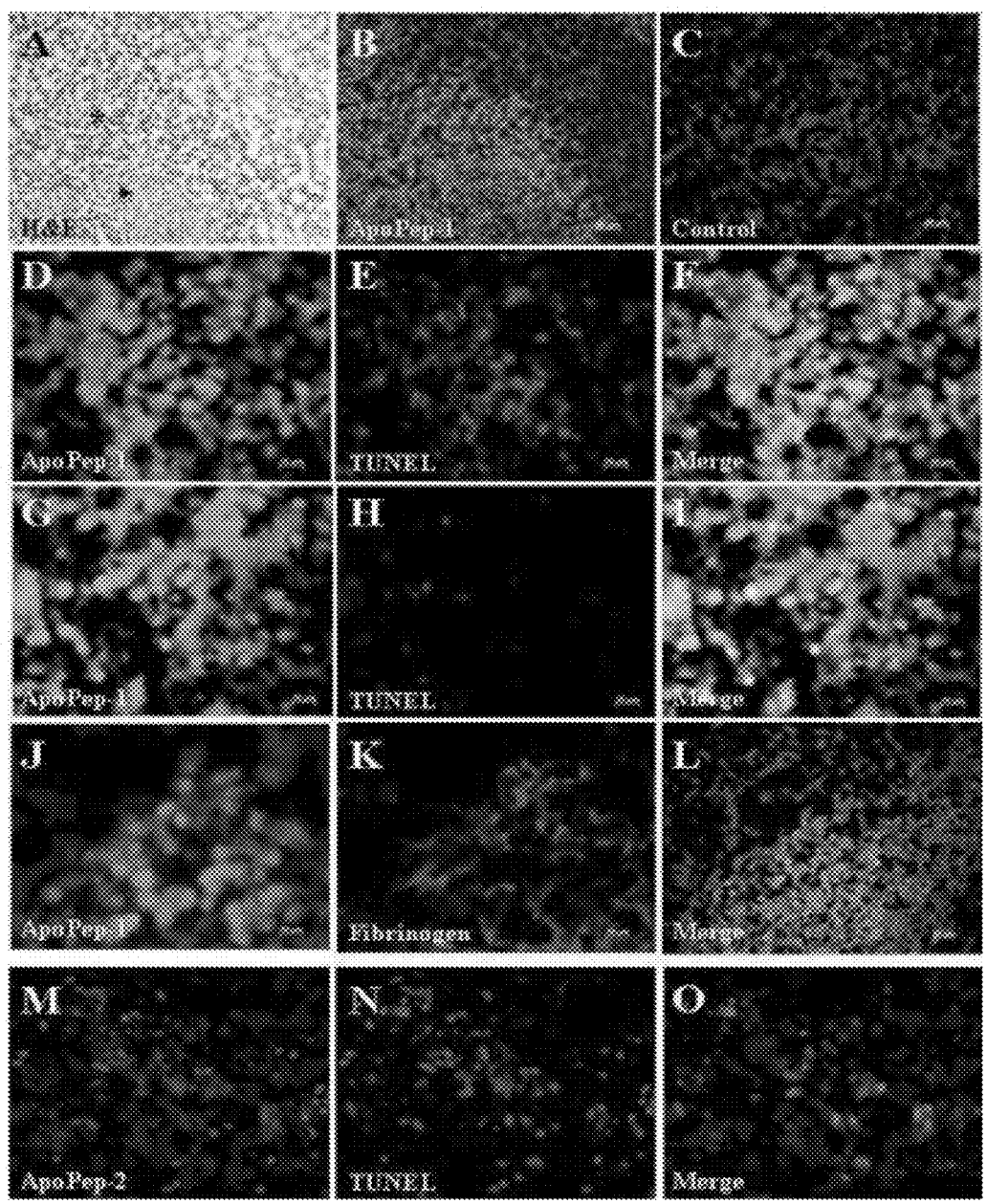
FIG. 2 shows the images obtained as follows. Into the tail vein of a nude mouse to which A549 tumor cells were xenotransplanted under the skin, the peptide of the present invention having an amino acid sequence represented by SEQ ID NO: 1 (ApoPep-1) and being linked with fluorescent label was injected. Images were obtained for H&E staining of the tumor tissue (A), fluorescence of the peptide (B, D, G, J), TUNEL staining (E, H), fibrinogen staining (K) and merge using a computer (F=D+E, I=G+H, L=J+K). C is a fluorescence image of a control peptide. D-F correspond to the location marked by the asterisk in A, and G-I correspond to the location marked by the triangle in A. Also, the same experiment was carried out for the peptide of the present invention having an amino acid sequence represented by SEQ ID NO: 2 (ApoPep-2), and images were obtained fluorescence of the peptide (M), TUNEL staining (N) and merge (O).

As a result, as seen in FIG. 2, tumors were identified by H&E staining (FIG. 2A). The peptide was observed in the tumor tissue when the peptide of the present invention (Apo-Pep-1) was injected (FIG. 2B), but it was hardly observed when the control peptide was injected (FIG. 2C). From the peptide fluorescence (FIG. 2D), TUNEL staining (FIG. 2E) and merge of them (FIG. 2F) at the location marked by the asterisk in FIG. 2A, it was confirmed that the peptide binds to the cells stained by TUNEL, i.e. the apoptotic cells. Further, from the peptide fluorescence (FIG. 2G), TUNEL staining (FIG. 2H) and merge of them (FIG. 2I) at the location marked by the triangle in FIG. 2A, it was confirmed that the peptide also binds to the cells not stained by TUNEL. From the peptide fluorescence (FIG. 2J), fibrinogen staining (FIG. 2K) and merge of them (FIG. 2L) for the location marked by triagle, it was confirmed that the location was coagulation necrotic site.

A similar experiment was performed for the peptide having an amino acid sequence represented by SEQ ID NO: 2 (Apo-Pep-2). From the peptide fluorescence (FIG. 2M), TUNEL staining (FIG. 2N) and merge of them (FIG. 2O), it was confirmed that the peptide binds to the apoptotic cells in the tumor tissue.

Example 3

Binding of the Peptide of the Present Invention to Cultured Apoptotic Cells

<3-1> Microscopic Observation of Binding of the Peptide to Apoptotic Cells

Cells were cultured in chamber slide (Nalgene Nunc) and treated with 50 μM etoposide (Sigma) for a given period of time (A549 and HeLa cells: for 15 hours, H460 cells: 24 hours, L132 cells: 3 hours, RAW cells: 6 hours) to induce apoptosis. The cells were cultured in RMPI-1640 medium (A549 and H460 cells) or DMEM (HeLa, L132 and RAW cells) containing antibiotics (penicillin and streptomycin) and 10% FBS. All the cells were subcultured every 3 or 4 days. The apoptosis-induced apoptotic cells were washed with PBS and blocked with 1% BSA at 37° C. for 30 minutes. Then, the cells were reacted with 10 μM of the peptide labeled with fluorescein, at 4° C. for 1 hour. After washing, the cells were reacted with an annexin V reaction buffer containing Alexa594-labeled annexin V (Molecular Probes), at room temperature for 15 minutes. The cells were washed with PBS and then fixed with 4% paraformaldehyde for 5 minutes. Thereafter, after counterstaining using the nuclear stain 4',6-diamidino-2-phenylindole (DAPI), followed by treatment with a mounting solution (Molecular Probes), images of the cells were obtained under a fluorescence microscope (Zeiss).

Figure 3:
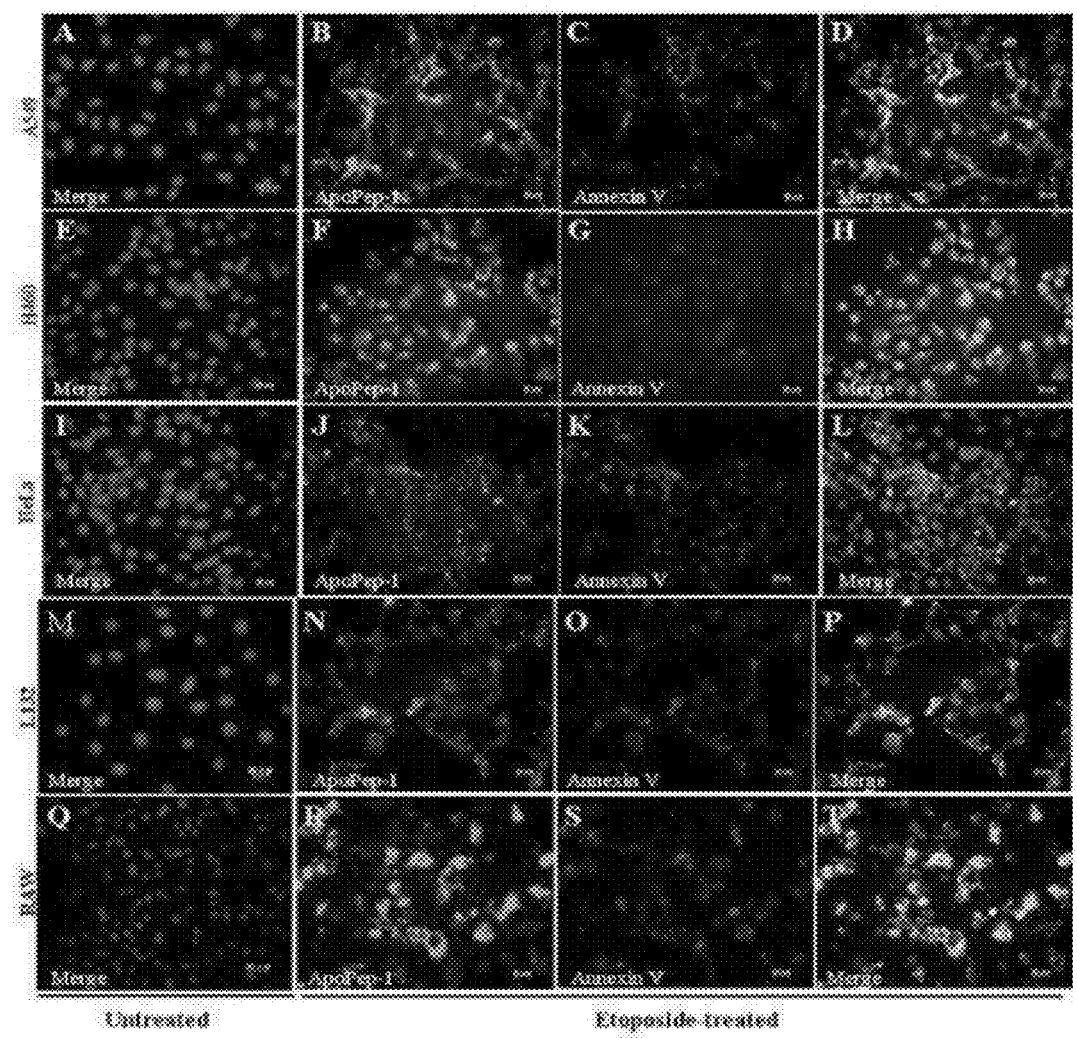
FIG. 3 shows the images obtained as follows. Apoptosis was induced in various cells (A549, H460, HeLa, L132, RAW) by treating with etoposide. Images were obtained for the fluorescence resulting from the binding with the peptide of the present invention (ApoPep-1) (B, F, J, N, R), annexin V staining of the cells (C, G, K, O, S) and merges thereof (D, H, L, P, T). A, E, I, M and Q are merge images of the cells in which apoptosis was not induced, as control group, of binding with the peptide of the present invention (ApoPep-1) or with annexin V.

As a result, as seen in FIG. 3, no labeling was observed when the normal cells, not treated with etoposide, were treated with the peptide of the present invention (ApoPep-1) and annexin V (first column in FIG. 3; A, E, I, M, O). In contrast, labeling was observed in the case of treating with the peptide of the present invention (ApoPep-1) (second column in FIG. 3; B, F, J, N, R) or with annexin V (third column in FIG. 3; C, G, K, O, S), to the etoposide-treated apoptotic cells. Through merge of the images using a computer program, it was confirmed that the bindings for both the peptide of the present invention and annexin V were at the same locations (fourth column in FIG. 3; D, H, L, P, T).

<3-2> Competitive Inhibition of Binding of the Peptide to Apoptotic Cells by Annexin V Treatment In order to further investigate the binding properties of the peptide of the present invention (ApoPep-1) to apoptotic cells, competitive inhibition by annexin V was measured. To this end, first, apoptotic A549 cells were pre-treated with annexin V, not labeled with fluorescence, at concentrations of 0, 200 and 1000 M. Then, after reacting the cells with fluorescence-labeled annexin V under the same condition as described in Example <3-1>, the binding of the cells was observed under a fluorescence microscope.

As a result, as seen in FIG. 4A-C, the fluorescence decreased significantly when annexin V, not labeled with fluorescence, was pre-treated at high concentration due to competitive inhibition of the binding with fluorescence-labeled annexin V.

Further, apoptotic A549 cells were pre-treated with annexin V, not labeled with fluorescence, at a concentration of 1000 μM. Then, after reacting the cells with fluorescence-labeled peptide under the same condition as described in Example <3-1>, the binding of the cells was observed under a fluorescence microscope.

Figure 4:
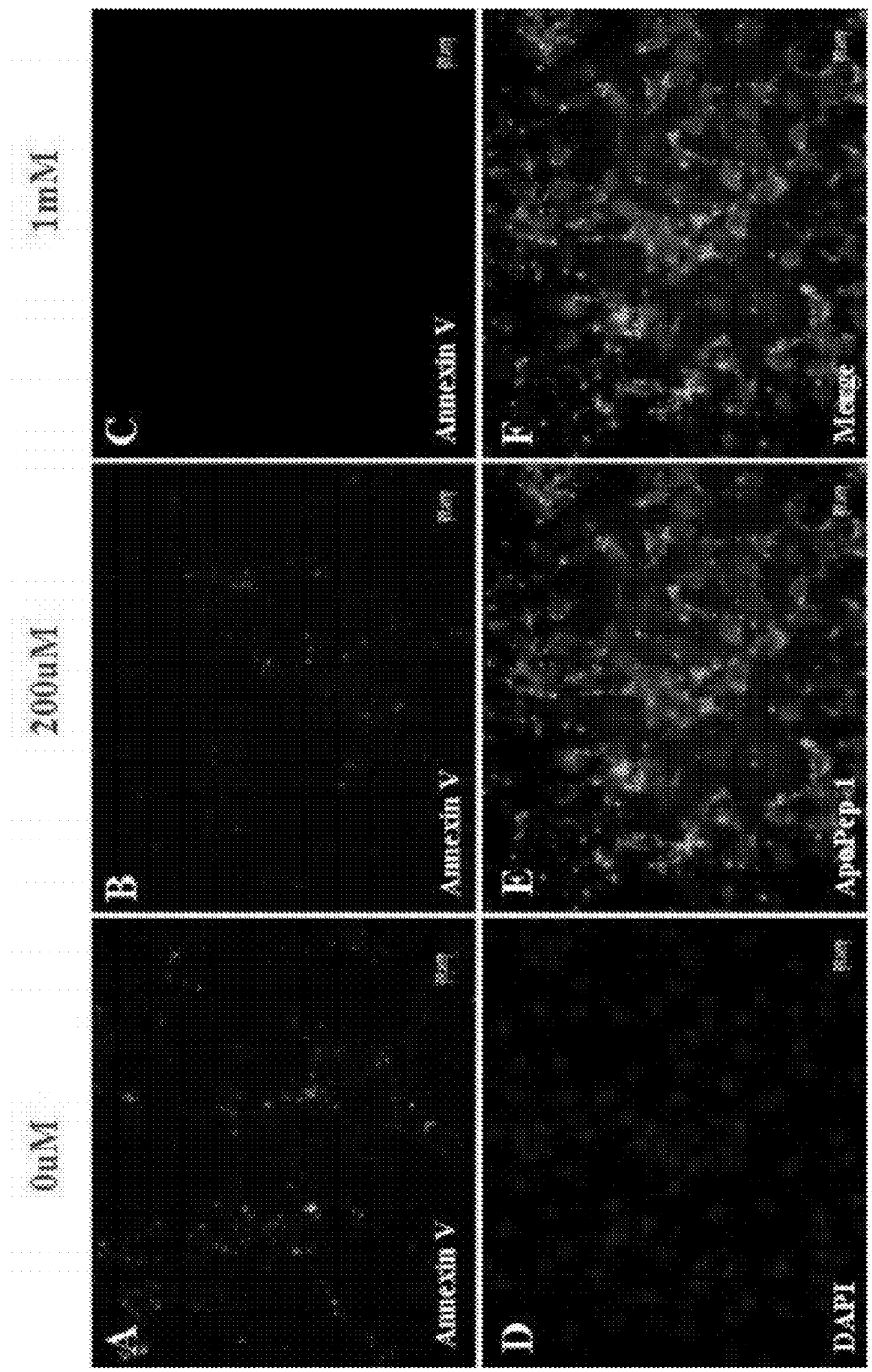
FIG. 4 shows the images obtained as follows. Apoptosis was induced in A549 tumor cell by treating with etoposide. Imaged were obtained by staining with red fluorescence-labeled annexin V after pre-treating with annexin V without a fluorescence label at concentrations of 0 μM (A), 200 μM (B) and 1000 μM (C). Further, after pre-treating with annexin V at 1000 μM, images were obtained for binding with the peptide of the present invention (ApoPep-1) (E), nuclear staining (D) and a merge thereof (F).

As a result, as seen in FIG. 4, D-F, the binding of the peptide of the present invention (ApoPep-1) was not inhibited by the treatment with annexin V at high concentration.

<3-3> Confirmation of Binding of the Peptide of the Present Invention to Apoptotic Cells Through FACs Analysis As another way of confirming the binding of the peptide of the present invention to apoptotic cells, apoptotic cells were treated with the peptide of the present invention, labeled with fluorescein, and the binding was confirmed through FACS analysis. First, apoptosis was induced by treating A549 cells with 50 μM etoposide for 6 to 15 hours. The apoptotic cells or normal cells were reacted with ApoPep-1 (5 μM), ApoPep-2 (10 μM) or a control peptide at the same concentrations, labeled with fluorescein, at 4° C. for 1 hour. Further, the cells were reacted with fluorescein-labeled annexin V at room temperature for 15 minutes. After staining the cells with propodium iodide (PI) simultaneously, followed by washing with PBS, FACS analysis was performed using a FACS instrument (Becton Dickinson).

Figure 5:
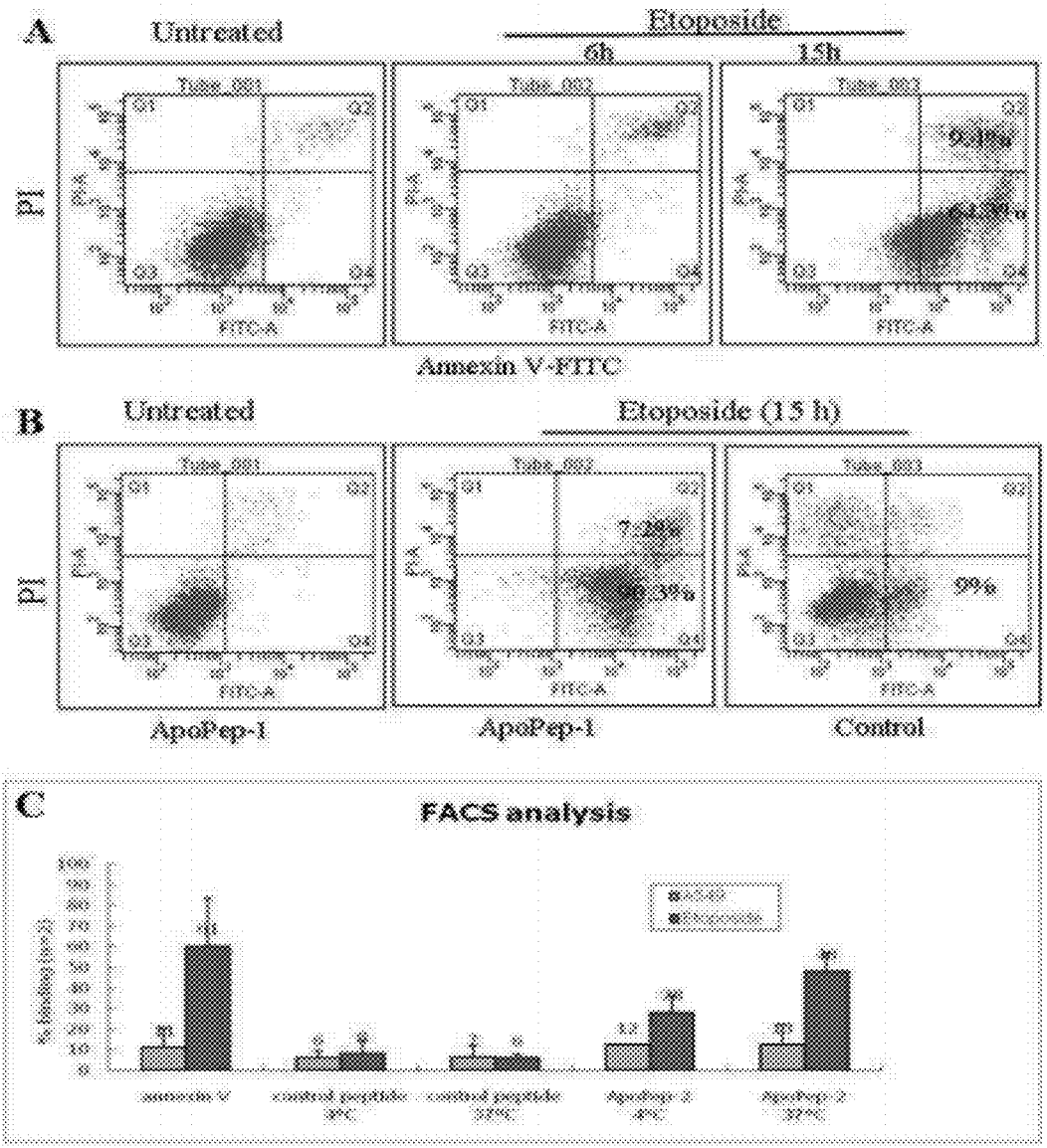
FIG. 5 shows FACS analysis result of binding of A549 tumor cells, treated with or without etoposide, with annexin V (A), and the peptide of the present invention (ApoPep-1) or a control peptide (Control) (B). The abscissa represents the degree of binding to annexin V or the peptide, and the ordinate represents the degree of propidium iodide (PI) staining. C shows FACS analysis result of binding of the cells with the peptide of the present invention (ApoPep-2) or the control peptide at 4° C. and 37° C. (A549: etoposide non-treated group; Etoposide: etoposide treated group).

As a result, as seen in FIG. 5, when the etoposide-treated apoptotic A549 cells were stained with annexin V and PI, the percentage of the cells stained only by annexin V (fraction Q4, early stage of apoptosis) and the percentage of the cells stained by both annexin V and PI (fraction Q2, later stage of apoptosis) were 64.3% and 9.4%, respectively, at 15 hours, which were higher than at 6 hours (FIG. 5A). Further, when the cells that had been treated with etoposide for 15 hours were treated with ApoPep-1, 90.3% and 7.2% of the cells at the early stage and later stage of apoptosis, respectively, were bound to the peptide (FIG. 5B). In contrast, when the apoptotic cells were treated with the control peptide or when the normal cells were treated with the peptide of the present invention (ApoPep-1), the binding was almost nonexistent.

Further, when the apoptotic A549 cells that had been treated with etoposide for 20 hours were treated with ApoPep-2 peptide, at 4° C. or 37° C. for 1 hour, the peptide bound better to the apoptotic cells than to the normal cells (FIG. 5C).

Example 4

Targeting of Apoptotic Cells in Tumor by the Peptide of the Present Invention and Imaging Thereof <4-1> Targeting of Apoptotic Cells in Tumor by the Peptide and Imaging Thereof.

Nude mice in which tumor was xenotransplanted using A549 cells were prepared as in Example <2-1>. The mice were grouped into a doxorubicin (Sigma) treated group (+Dox) and untreated group (−Dox). The treated group was treated with doxorubicin (10 mg/kg) 3 times, with an interval of 48 hours, a week prior to injection of the peptide. At the tail vein of each mouse, the peptide of the present invention or a control peptide, labeled with fluorescein, was injected at a final concentration of 50 µM, under isoflurane anesthesia. Following the injection, in vivo fluorescence images were obtained every hour, from 1 hour to 6 hours after the injection, using an Optix exPlore instrument (GE Healthcare). The images were standardized using the software provided with the instrument.

Further, when the tumor grew considerably (1 cm or larger in diameter), the peptide of the present invention was injected at the same concentration as above, without doxorubicin treatment, and in vivo fluorescence images were obtained at every given time using an IVIS fluorescence imaging system (Chemipro).

Figure 6:
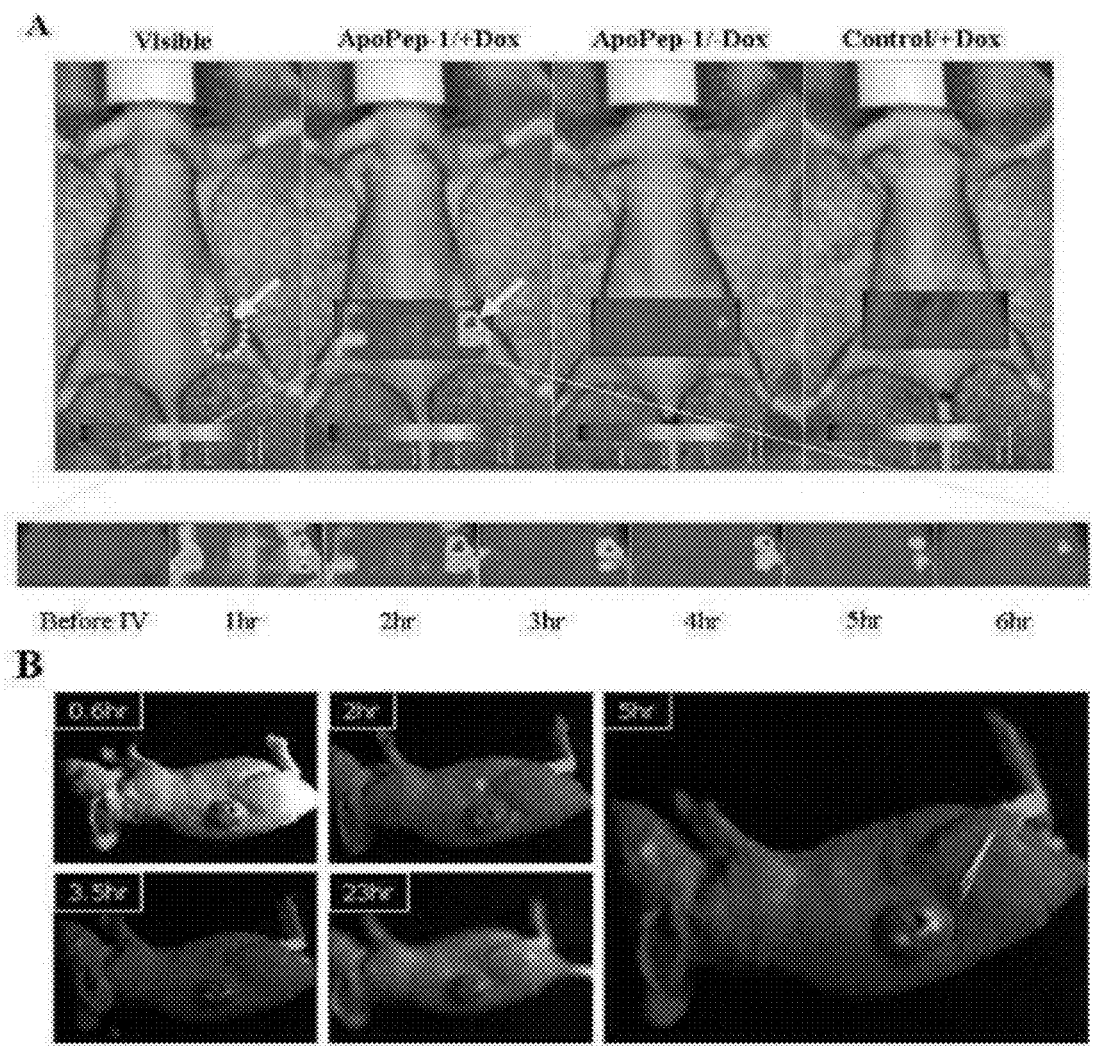
FIG. 6 shows the images obtained as follows. A nude mouse to which a tumor was xenotransplanted was treated with or without doxorubicin. 24 hours later, the peptide having an amino sequence represented by SEQ ID NO: 1 (ApoPep-1) (A) and the peptide having an amino sequence represented by SEQ ID NO: 2 (ApoPep-2) (B), which were labeled with fluorescence, were injected into blood. The peptides were traced in vivo based on fluorescence.

As a result, as seen in FIG. 6A, when ApoPep-1 was injected to the doxorubicin treated group, the fluorescence signal from the tumor tissue by fluorescein was the most strongly detected at 2 hours, and the signal was detected until at 5 hours. In contrast, when the peptide of the present invention was injected to the doxorubicin untreated group or when the control peptide was injected to the doxorubicin treated group, the fluorescence signal was weakly detected or almost nonexistent.

Further, as seen in FIG. 6B, when ApoPep-2 was injected to a mouse with a large tumor (1 cm or larger in diameter), the fluorescence from the tumor was detected from 2 hours. A strong fluorescence signal was detected at 5 hours. This implies that in the large-sized tumor, apoptosis occurred significantly in the tumor tissue in spite of the absence of treatment of an agent.

<4-2> Radionuclide Imaging of Targeting of Apoptotic Cells in Tumor by the Peptide Nude mice in which tumor was xenotransplanted using H460 cells were prepared as in Example <2-1>. The mice were grouped into a doxorubicin (Sigma) treated group and untreated group. The treated group was treated with doxorubicin (10 mg/kg) 3 times, with an interval of 48 hours, a week prior to injection of the peptide. The peptide of the present invention (ApoPep-1), labeled with the radioactive isotope $^{124}I$, was injected through the tail vein of each mouse under isoflurane anesthesia (treated group: 91 µCi; untreated group: 93 µCi). Further, $^{18}F$-labeled FDG, which is frequently used for PET, was injected to the doxorubicin treated group and untreated group, at 300 µCi and 304 µCi, respectively. Radionuclide images were obtained using a micro PET instrument (Concorde MicroSystems) 5 hours after the injection of [$^{124}I$] ApoPep-1 and 1 hour after the injection of [$^{18}F$]FDG.

Figure 7:
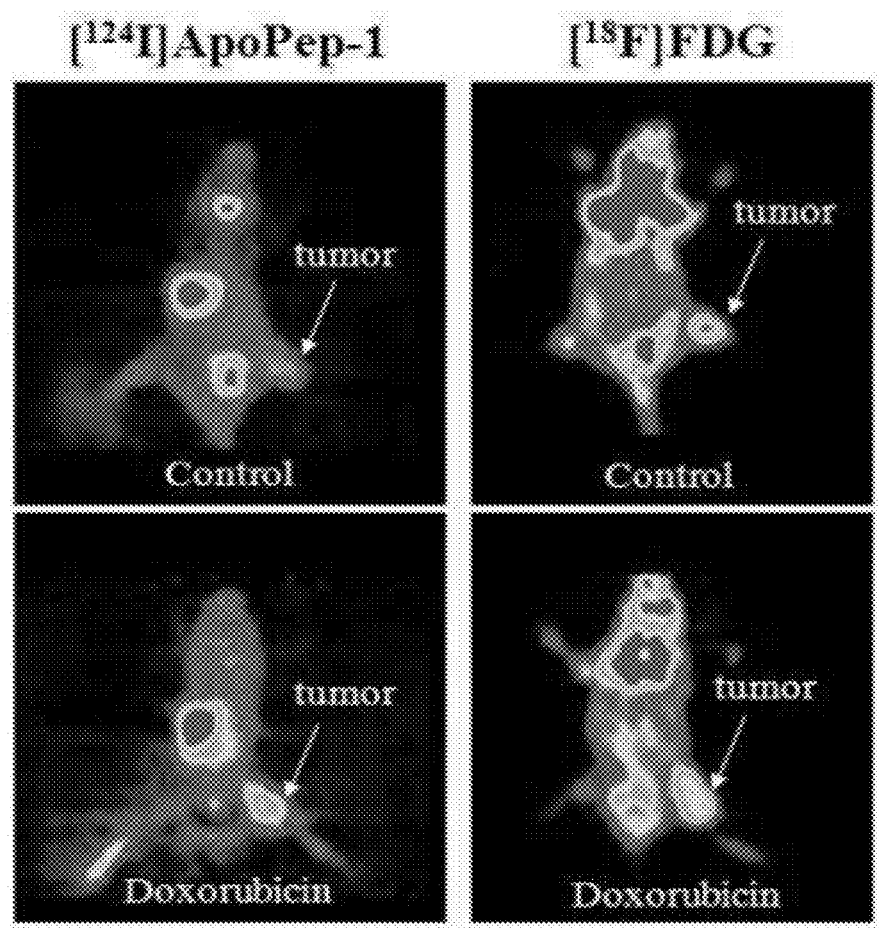
FIG. 7 shows the images obtained as follows. A nude mouse to which a tumor was xenotransplanted was treated with doxorubicin. 24 hours later, $^{18}$F-labeled FDG and the peptide having an amino sequence represented by SEQ ID NO: 1 (ApoPep-1), which was labeled with $^{124}$I-labeled, were injected into blood. They were traced in vivo using a micro PET.

As a result, as seen in FIG. 7, when [124I]ApoPep-1 was injected, a much stronger signal was observed at the tumor site in the doxorubicin treated group as compared with the untreated group. In contrast, for [$^{18}F$]FDG, a weaker signal was observed in the doxorubicin treated group as compared with the untreated group. This implies that the peptide of the present invention is capable of recognizing and monitoring the apoptosis of tumor cells induced by the anticancer drug treatment.

Example 5

Molecular Imaging of Arteriosclerosis Using the Peptide of the Present Invention An arteriosclerotic animal model was established by feeding mice, in which low-density lipoprotein (LDL) receptor was deficient (Ldlr(−/−)) genetically, with a high-cholesterol diet for 8 weeks. At the tail vein of the arteriosclerotic mouse and normal mouse, the peptide having an amino sequence represented by SEQ ID NO: 1 (ApoPep-1) or a control peptide, labeled with Cy7.5 NIR fluorescence, was injected at a final concentration of 50 µM, under isoflurane anesthesia. Two hours later, with the mouse anesthetized, in vivo images of the NIR fluorescence were obtained using an Optix exPlore instrument. Following the in vivo imaging, NIR fluorescence was measured in vitro after isolating the aorta.

Figure 8:
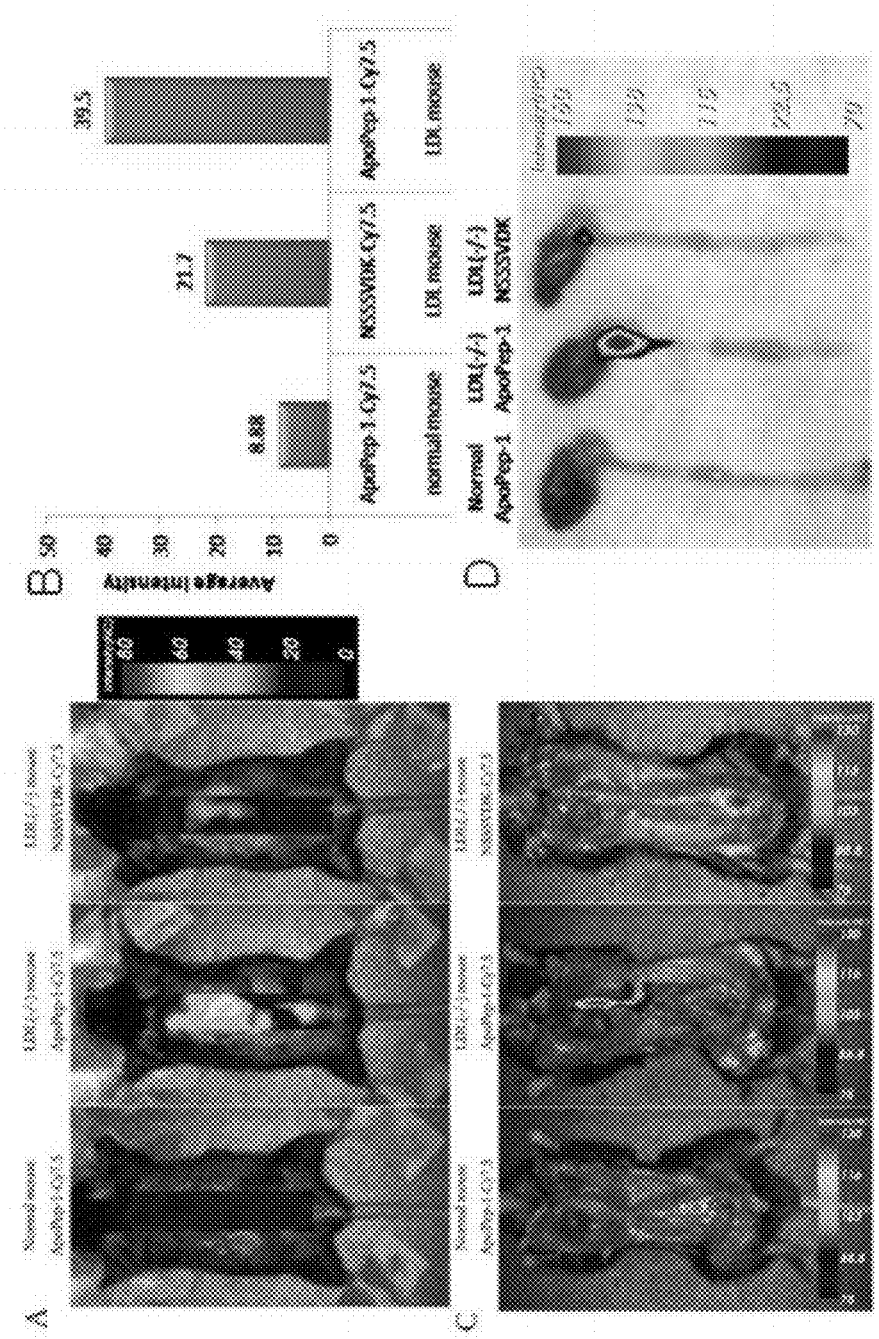
FIG. 8 shows the images obtained as follows. To an arteriosclerosis model mouse in which low-density lipoprotein (LDL) receptor was deleted genetically (Ldlr (−/−)) and a normal mouse, the peptide having an amino sequence represented by SEQ ID NO: 1 (ApoPep-1), which was labeled with Cy7.5 near infrared (NIR) fluorescence, was intravenously injected. One hour later, NIR images were obtained from the back (A) or after exposing the aorta by cutting the abdomen open (C). B shows the intensity of NIR in A. D shows NIR images of the aorta isolated from each mouse (ApoPep-1-Cy7.5: Cy7.5-labeled ApoPep-1; NSSSVDK-Cy7.5: Cy7.5-labeled control peptide).

As a result, when the images were obtained from the back, a stronger NIR fluorescence was observed in the arteriosclerotic mouse to which ApoPep-1 was injected than the mouse to which the control peptide was injected. Fluorescence was almost nonexistent in the normal mouse, despite the injection of ApoPep-1 (FIG. 8A). The intensity of the fluorescence due to the peptide of the present invention was about two times that of the control peptide (FIG. 8B). When the images were obtained after exposing the aorta by cutting the abdomen open, the NIR fluorescence was much stronger in the arteriosclerotic mouse to which ApoPep-1 was injected as compared with that to which the control peptide was injected (FIG. 8C). A similar result was obtained when the fluorescence was measured in vitro after isolating the aorta (FIG. 8D).

Example 6

Molecular Imaging of Stroke Using the Peptide of the Present Invention

A stroke model was established by occluding the left middle cerebral artery of a rat for 2 hours, followed by reperfusion. Two hours after the reperfusion, the peptide having an amino sequence represented by SEQ ID NO: 1 (ApoPep-1) and a control peptide, labeled with Cy7.5 NIR fluorescence, was intravenously injected at a final concentration of 50 µM to the stroke rat and a normal rat through the tail vein, under isoflurane anesthesia. One and three hours after the intravenous injection, NIR images of the head portion were obtained. Further, NIR fluorescence images of the brains of the rats of the 3 hour group were obtained.

Figure 9:
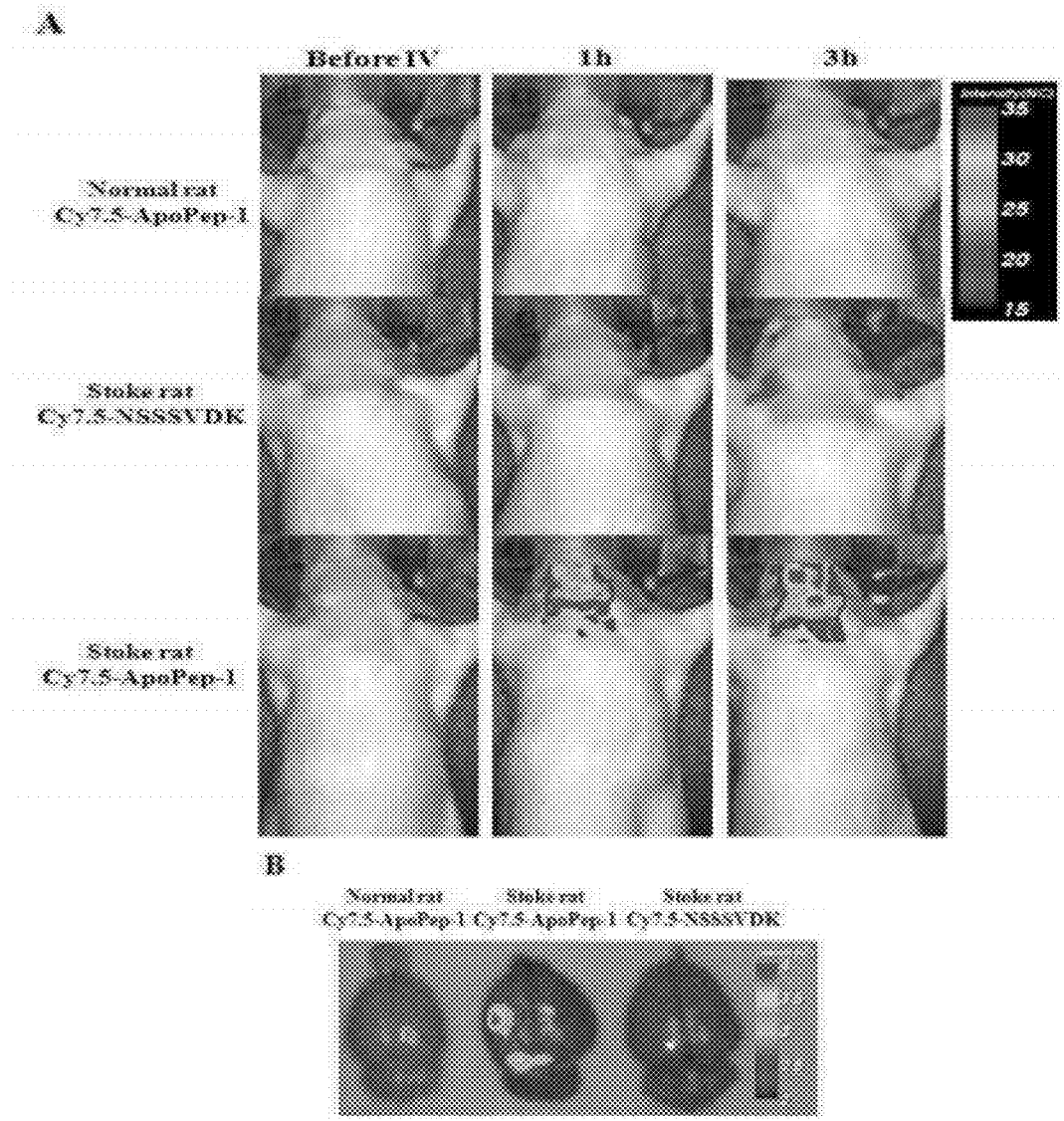
FIG. 9 shows the images obtained as follows. To a stroke rat model, which was subjected to 2 hours of middle cerebral artery occlusion followed by reperfusion, and a normal rat, the peptide having an amino sequence represented by SEQ ID NO: 1 (ApoPep-1), which was labeled with Cy7.5 NIR fluorescence, was intravenously injected. One and three hours later, NIR images of the head portion were obtained (A). Then, NIR images of the brains of the rats of the 3 hour group were obtained (B) (ApoPep-1-Cy7.5: Cy7.5-labeled ApoPep-1; NSSSVDK-Cy7.5: Cy7.5-labeled control peptide).

As a result, NIR fluorescence was observed at 1 hour at the head portion of the stroke rat to which the peptide of the present invention (ApoPep-1) was injected, and a very strong fluorescence was observed at 3 hours. In contrast, fluorescence was almost nonexistent in the stroke rat to which the control peptide (NSSSVDK) was injected or in the normal rat to which ApoPep-1 was injected (FIG. 9A). A similar result was obtained when the brains were isolated from the rats and fluorescence was observed in vitro. Especially, fluorescence was observed at the left hemisphere of the stroke rat, since the left middle cerebral artery had been occluded (FIG. 9B).

Example 7

Molecular Imaging of Myocardial Ischemia Using the Peptide of the Present Invention A myocardial ischemia model was established by occluding the coronary artery of a rat, followed by reperfusion (ischemia/reperfusion model). For the operation, a rat was anesthetized by intra-abdominally injecting 10 mg of phenobarbital and, followed by endobronchial intubation, a ventilator was connected. Thereafter, the thorax was cut open to expose the heart. The left anterior descending coronary artery was occluded for 30 minutes using a suture and, then, the blood was allowed to circulate. For a control group (Sham), the same operation was performed, except for the occlusion.

Two hours after the reperfusion, the peptide having an amino sequence represented by SEQ ID NO: 1 (ApoPep-1), labeled with Cy7.5 NIR fluorescence, was intravenously injected to the rats of the myocardial ischemia group and the control group. Two hours after the peptide injection, NIR images of the heart portion were obtained. Then, NIR images were obtained after isolating the heart.

Figure 10:
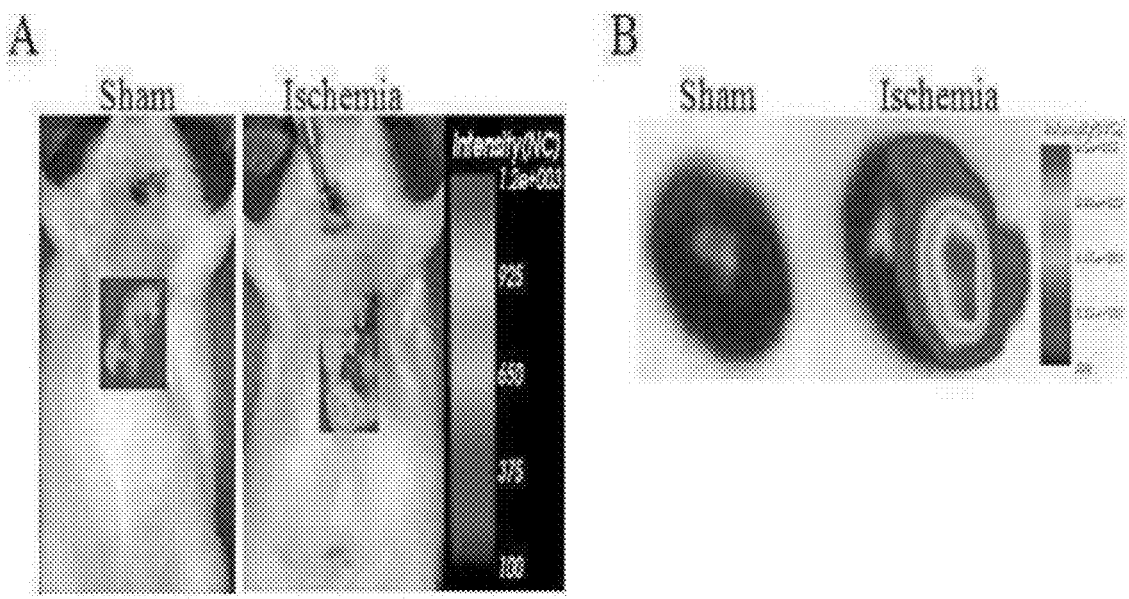
FIG. 10 shows the images obtained as follows. To a myocardial ischemic rat and a control rat (Sham), the peptide having an amino sequence represented by SEQ ID NO: 1 (ApoPep-1), which was labeled with Cy7.5 NIR fluorescence, was intravenously injected. Two hours later, NIR images of the heart portion were obtained (A). Then, NIR images of the hearts of the rats were obtained (B).

As a result, a much stronger NIR fluorescence was observed in the myocardial ischemic rat than in the control group rat (FIG. 10A). A similar result was obtained when the fluorescence was measured in vitro after isolating the heart (FIG. 10B).

As can be seen the foregoing, the peptide of the present invention may be capable of specific binding with the apoptotic cells. Accordingly, the peptide of the present invention may be useful for detection of apoptotic cells in tumor, for detection of apoptotic cells in myocardial infarction, stroke or arteriosclerosis site, for imaging of diagnosis or target drug delivery and so on.

Example 8

Histological Evaluation of In Vivo Tumor Targeting by the Peptide of the Present Invention <8-1> Preparation of Tumor Xenotransplantation Model of Nude Mouse All animal experiments were performed in accordance with the guideline of the Institutional Animal Care and Use Committee. For tumor xenotransplantation, human lung cancer cells (A549, 1×10$^6$ cells) suspended in RMPI-1640 medium was subcutaneously injected at the right upper or lower limb of a 6-week-old male BALB/c nude mouse (Hyochang Science). Then, 3 to 4 weeks were given for the tumor to grow to a size of 0.5 to 1 cm. The A549 cell line used in the experiment was cultured in RMPI-1640 medium containing 10% fetal bovine serum (FBS) in which antibiotics (penicillin and streptomycin) were included. Subculturing was performed every 3 or 4 days.

<8-2> Histological Analysis of Tumor Targeting

The peptides used in the present invention were fluorescein-attached form at the N-terminal. They were synthesized according to the standard Fmoc technique and then isolated through HPLC. The peptide synthesis was performed by an expertise company (Peptron).

The polypeptide of the present invention (ApoPep-2) or a control peptide (amino acid sequence: NSSSVDK), labeled with fluorescein, was injected into the tail vein of a mouse under isoflurane anesthesia, to a final concentration of 50 µM, and 2 hours was given for circulation.

For histological analysis, the mouse was anesthetized and the abdomen was cut open. After sequentially perfusing phosphate-buffered saline (PBS) and 4% paraformaldehyde through the heart, tumor tissues and organs were removed. Each tissue was frozen and cryosected. Apoptosis in the tumor tissue was confirmed by TUNEL (in vitro terminal deoxynucleotidyl transferase-mediated dUTP nick-end labeling) assay according to the instructions of the manufacturer (Chemicon). After treatment with a mounting solution containing the nuclear stain 4',6-diamidino-2-phenylindole (DAPI) (Invitrogen), images of the cells were obtained under a fluorescence microscope (Zeiss).

Figure 11:
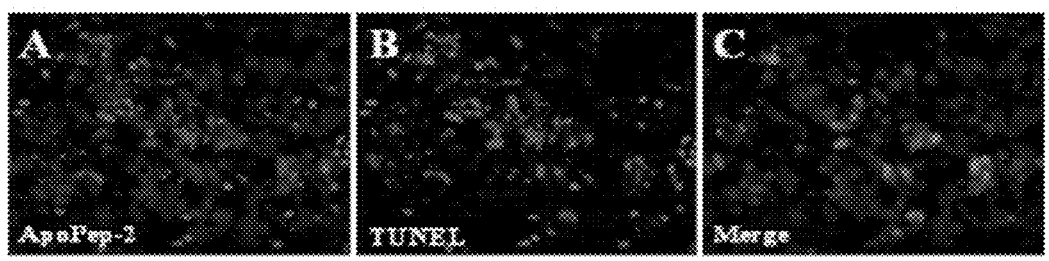
FIG. 11 shows the images obtained as follows. Into the tail vein of a nude mouse to which A549 tumor cells were xenotransplanted under the skin, the polypeptide of the present invention having an amino acid sequence represented by SEQ ID NO: 2 (ApoPep-2) and being linked with fluorescent label was injected. Images were obtained for the fluorescence of the peptide (A), TUNEL staining (B) and merge (C). Shown in blue is DAPI nuclear staining.

As a result, as seen in FIG. 11, the peptide was observed in the tumor tissue when the polypeptide of the present invention (ApoPep-2) was injected (FIG. 11A). From the peptide fluorescence (green, FIG. 11A), TUNEL staining (red, FIG. 11B) and merge of them (FIG. 11C), it was confirmed that the peptide binds to the cells stained by TUNEL, i.e. the apoptotic cells, in the tumor tissue. Shown in blue is DAPI nuclear staining.

Example 9

Binding of the Polypeptide of the Present Invention to Cultured Apoptotic Cells

<9-1> Microscopic Observation of Binding of the Peptide to Apoptotic Cells

Cells were cultured in chamber slide (Nunc) and treated with 50 µM etoposide (Sigma) for 16 hours (A549 cells) or 50 ng/ml trail (R&D Systems) for 16 hours (MDA-MB231 cells) to induce apoptosis. The cells were cultured in RMPI-1640 medium (A549 cells) or DMEM-High (MDA-MB231 cells) containing antibiotics (penicillin and streptomycin) and 10% FBS. All the cells were sub-cultured every 3 or 4 days. The apoptosis-induced apoptotic cells were washed with PBS and blocked with 1% BSA at 37° C. for 30 minutes. Then, the cells were reacted with 10 µM of the peptide labeled with fluorescein, at 4° C. for 1 hour. After washing, the cells were reacted with an annexin V reaction buffer containing Alexa594-labeled annexin V (Invitrogen) at room temperature for 15 minutes. The cells were washed with PBS and then fixed with 4% paraformaldehyde for 5 minutes. After treatment with a mounting solution containing the DAPI nuclear stain, images of the cells were obtained under a fluorescence microscope.

Figure 12:
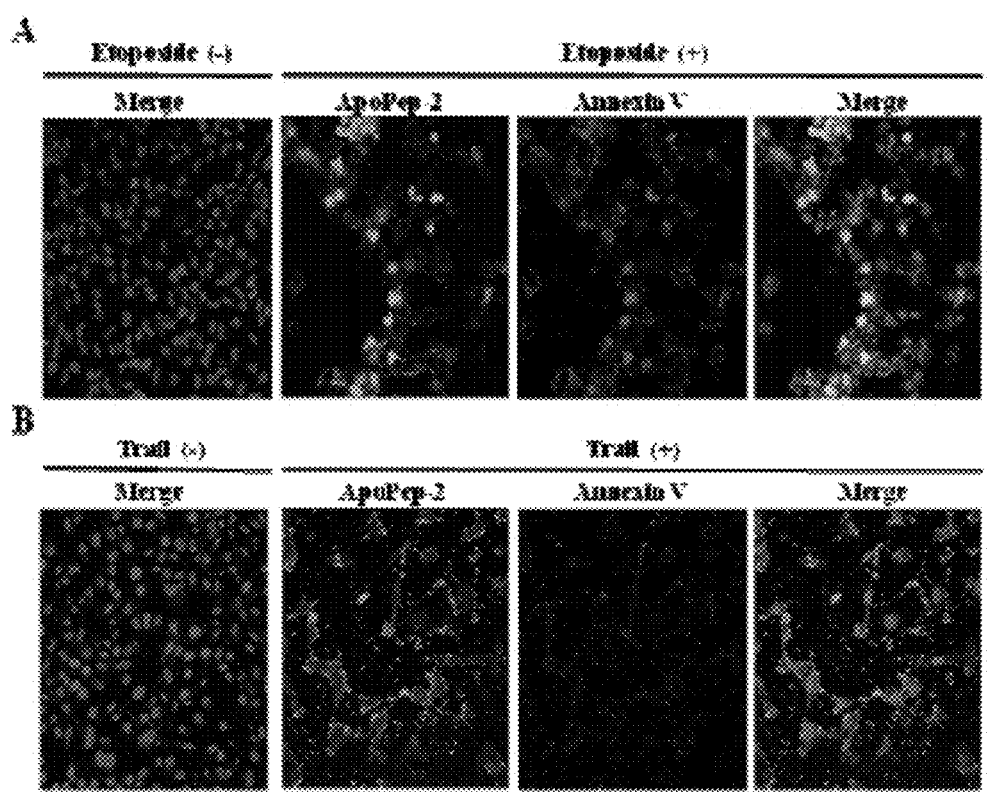
FIG. 12 shows the images obtained as follows. Apoptosis was induced in A549 cells by treating with etoposide (FIG. 12A) or MDA-MB231 cells by treating with trail (FIG. 3B). Images were obtained for the fluorescence resulting from the binding with the polypeptide of the present invention (ApoPep-2) (green, second column in FIG. 12; A, B), annexin V staining of the cells (red, third column in FIG. 12; A, B) and merges thereof plus DAPI nuclear staining (blue) (fourth column in FIG. 12; A, B). Images (first column in FIG. 12; A, B) are merge images of the cells in which apoptosis was not induced, as control group, of binding with ApoPep-2 and annexin V plus DAPI staining.

As a result, as seen in FIG. 12, no labeling was observed when A549 or MDA-MB231 cells that were not treated with etoposide or trail, respectively, were treated with the polypeptide of the present invention (ApoPep-2) and annexin V (first column in FIG. 12; A, B). In contrast, labeling was observed in the case of treating A549 or MDA-MB231 cells with ApoPep-2 (green, second column in FIG. 12; A, B) or with annexin V (red, third column in FIG. 12; A, B), to the etoposide- or trail-treated apoptotic cells, respectively. Through merge of the images and DAPI staining (blue) using a computer program, it was confirmed that the bindings for both the polypeptide of the present invention and annexin V were at the same locations (fourth column in FIG. 12; A, B).

<9-2> Competitive Inhibition of Binding of the Peptide to Apoptotic Cells by Annexin V Treatment In order to further investigate the binding properties of the polypeptide of the present invention (ApoPep-2) to apoptotic cells, competitive inhibition by annexin V was measured. To this end, first, apoptotic A549 cells were pre-treated with annexin V, not labeled with fluorescence, at concentrations of 0, 500 and 1000 µM. Then, after reacting the cells with fluorescence-labeled annexin V under the same condition as described in Example <9-1>, the binding of the cells was observed under a fluorescence microscope.

Figure 13:
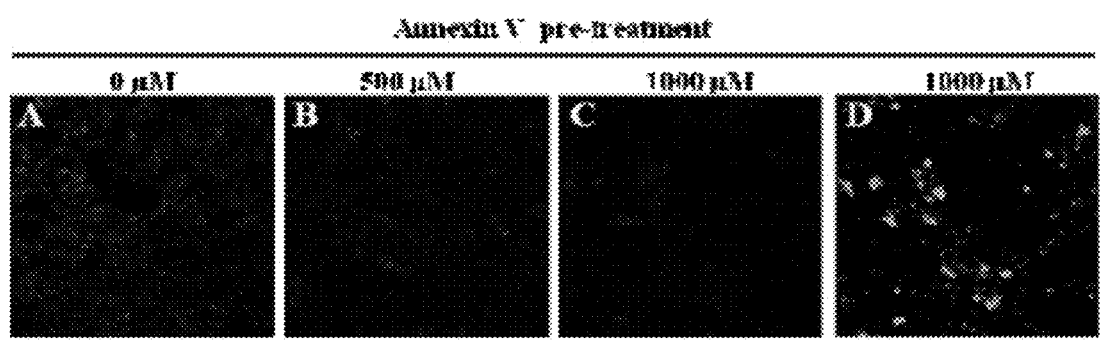
FIG. 13 shows the images obtained as follows. Apoptosis was induced in A549 tumor cell by treating with etoposide. Images were obtained by staining with red fluorescence-labeled annexin V after pre-treating with annexin V without a fluorescence label at concentrations of 0 μM (A), 500 μM (B) and 1000 μM (C). Further, after pre-treating with annexin V at 1000 μM, images were obtained for binding with the polypeptide of the present invention (ApoPep-2) (D).

As a result, as seen in FIG. 13A-C, the fluorescence decreased significantly when annexin V, not labeled with fluorescence, was pre-treated at high concentration due to competitive inhibition of the binding with fluorescence-labeled annexin V.

Further, apoptotic A549 cells were pre-treated with annexin V, not labeled with fluorescence, at a concentration of 1000 µM. Then, after reacting the cells with fluorescence-labeled peptide under the same condition as described in Example <9-1>, the binding of the cells was observed under a fluorescence microscope.

As a result, as seen in FIG. 13D, the binding of the polypeptide of the present invention (ApoPep-2) was not inhibited by the treatment with annexin V at high concentration.

<9-3> FACs Analysis of Binding of the Polypeptide of the Present Invention to Apoptotic Cells As another way of confirming the binding of the polypeptide of the present invention (ApoPep-2) to apoptotic cells, apoptotic cells were treated with the peptide, labeled with fluorescein, and the binding was confirmed through FACS analysis. First, apoptosis was induced by treating A549 cells with 50 μM etoposide for 20 hours. The apoptotic cells or normal cells were reacted with ApoPep-2 (10 μM) or a control peptide at the same concentration, labeled with fluorescein, at 4° C. or 37° C. for 1 hour. Further, the cells were reacted with fluorescein-labeled annexin V at room temperature for 15 minutes. After washing cells with PBS, FACS analysis was performed using a FACS instrument (Becton Dickinson).

Figure 14:
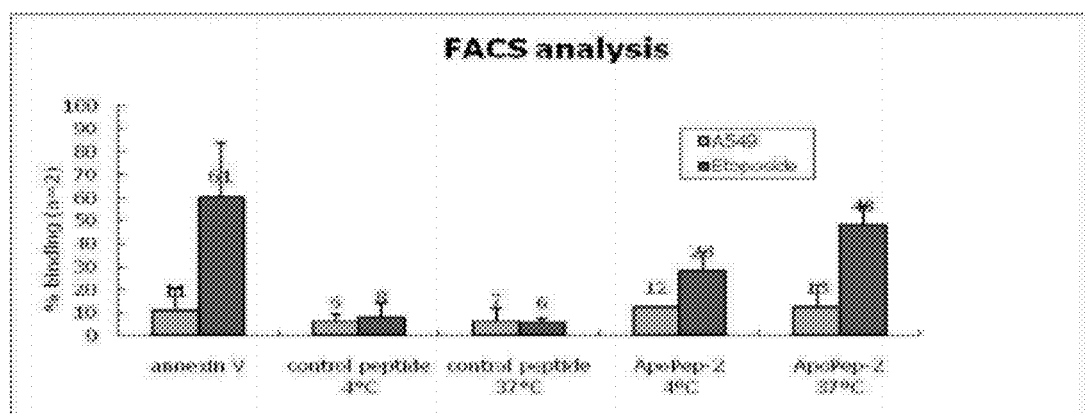
FIG. 14 shows FACS analysis result of percent binding of A549 tumor cells, treated with or without etoposide, with fluorescence-labeled annexin V at room temperature, or with the polypeptide of the present invention (ApoPep-2) or a control peptide at 4° C. and 37° C. (A549: etoposide non-treated group; Etoposide: etoposide treated group).

As a result, as seen in FIG. 14, when the etoposide-treated apoptotic A549 cells were stained with annexin V, the percentage of the cells stained by annexin V were 61%. Further, when the cells that had been treated with etoposide were treated with ApoPep-2 at 4° C. or 37° C. for 1 hour, 28% and 48% of the cells, respectively, were bound to the peptide. In contrast, when the apoptotic cells were treated with the control peptide or when the normal cells were treated with the peptide of the present invention, the binding was almost non-existent or minimal.

<9-4> Microscopic Observation of Binding of the Peptide to Necrotic Cells

A549 Cells were cultured in chamber slide (Nunc) and treated with glucose-depleted medium for 24 hours to induce necrosis. The necrosis-induced cells were washed with PBS and blocked with 1% BSA at 37° C. for 30 minutes. Then, the cells were reacted with 10 μM of the peptide labeled with fluorescein, at 4° C. for 1 hour. After washing, the cells were reacted with 1 mg/ml Hoechst 33324 dye and 5 mg/ml PI at 37° C. for 15 minutes. The cells were washed with PBS and then fixed with 4% paraformaldehyde for 5 minutes. Following treatment with a mounting solution (Invitrogen), cells were observed at 340/425 nm (for Hoechst) and 580/630 nm (for PI) by a fluorescence microscope (Zeiss).

Figure 15:
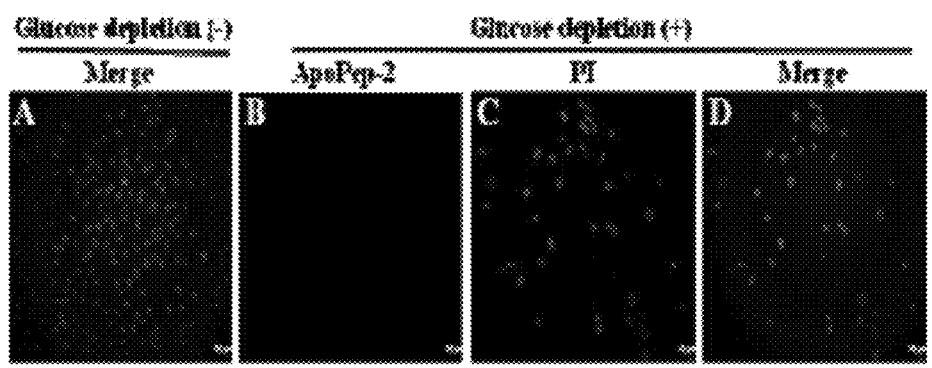
FIG. 15 shows the images obtained as follows. Necrosis was induced in A549 tumor cells by treating with glucose-depleted medium for 24 hours. Images were obtained by staining with green fluorescence-labeled peptide of the present invention (ApoPep-2) (B), PI (red, C), and merges thereof plus Hoechst nuclear staining (D). A is merge image of ApoPep-2 and PI plus Hoechst nuclear staining.

As a result, as seen in FIG. 15, only Hoechst staining was observed when A549 cells, that were not treated with glucose-depleted medium, were treated with the polypeptide of the present invention (ApoPep-2) and PI (FIG. 15A). Labeling was observed in the case of treating A549 cells with PI (FIG. 15C) to the glucose-depleted necrotic cells. In contrast, no labeling was observed with the polypeptide of the present invention (FIG. 15B). Through merge of the images using a computer program, it was also demonstrated that the bindings for the polypeptide of the present invention were not observed (FIG. 15D).

Example 10

Targeting of Apoptotic Cells in Tumor by the Polypeptide of the Present Invention and Imaging Thereof <10-1> Targeting of Apoptotic Cells in Tumor by the Peptide and Imaging Thereof.

Nude mice in which tumor was xenotransplanted using A549 cells were prepared as in Example <8-1>. The mice were grouped into a doxorubicin (Sigma) treated group (Dox+) and untreated group (Dox−). The treated group was treated with doxorubicin (5 mg/kg) one time, 12 hours prior to injection of the peptide. At the tail vein of each mouse, the polypeptide of the present invention or a control peptide, labeled with fluorescein or Cy7.5 near-infrared fluorescent dye, was injected at a final concentration of 50 μM, under isoflurane anesthesia. Following the injection, in vivo fluorescence images were obtained 0.5 hours and every hour, from 1 hour to 4 hours, after the injection, using an Optix exPlore instrument (ART). The images were standardized using the software provided with the instrument.

As a result, as seen in FIG. 16A, when the polypeptide of the present invention (ApoPep-2), that was labeled with fluorescein, was injected to a mouse with a large tumor (1 cm or larger in diameter), the fluorescence from the tumor was detected from 2 hours. A strong fluorescence signal was detected at 5 hours. This implies that in the large-sized tumor, apoptosis occurred significantly in the tumor tissue in spite of the absence of treatment of an agent.

As seen in FIG. 16B, when ApoPep-2, that was labeled with Cy7.5 dye, was injected to the doxorubicin treated group, the fluorescence signal from the tumor tissue was the most strongly detected at 2 hours. In contrast, when ApoPep-2 was injected to the doxorubicin untreated group or when the control peptide was injected to the doxorubicin treated group, the fluorescence signals were weakly detected.

Further, as seen in FIG. 16C, when tumor and other organs were isolated at 4 hours after the peptide injection and observed ex vivo, the fluorescence signal from the tumor of the doxorubicin treated group injected with ApoPep-2 was strong compared to the tumor of the doxorubicin untreated group injected with ApoPep-2 or the doxorubicin treated group injected with control peptide. The fluorescence signals from the kidney of all the groups were strong due to the renal clearance of peptides.

The invention claimed is:

1. A composition for detecting apoptotic cells comprising:
   (i) an isolated polypeptide consisting of the sequence (I) Cys-X1-Val-Ala-Pro-X2; and
   (ii) a labeling agent bound to the polypeptide of (i) selected from the group consisting of a coloring enzyme, a radioactive isotope, and a fluorescer,
   wherein X1 is an amino acid with polar uncharged side chain and X2 is an amino acid with positive charged side chain, and
   wherein the coloring enzyme is peroxidase or alkaline phosphatase; the radioactive isotope is selected from the group consisting of 18F, 124I, 125I, 32P, and 35P; and the fluorescer is selected from the group consisting of Fluorescein isothiocyanate (FITC), Rhodamine isothiocyanate (RITC), Green Fluorescent Protein (GFP), Enhanced Green Fluorescent Protein (EGFP), Red Fluorescent Protein (RFP), *Discosoma* sp. Red Fluorescent Protein (DsRed), Cyan Fluorescent Protein (CFP), Cyan Green Fluorescent Protein (CGFP), YFP (Yellow Fluorescent Protein), Cy3, Cy5, and Cy7.5.

2. A method for detecting apoptotic cells comprising the steps of:
   (a) mixing the polypeptide of claim 1 with a sample;
   (b) removing unbound or unspecifically bound polypeptide; and
   (c) detecting the binding and the location of the polypeptide.

3. A pharmaceutical composition for treating neoplastic disease comprising:
   (i) an isolated polypeptide consisting of the sequence (I) Cys-X1-Val-Ala-Pro-X2; and
   (ii) an antitumor agent bound to the polypeptide of (i) as an effective ingredient;
   wherein X1 is an amino acid with polar uncharged side chain and X2 is an amino acid with positive charged side chain,
   wherein the neoplastic disease is selected from the group consisting of colon cancer, lung cancer, stomach cancer, esophageal cancer, pancreatic cancer, gallbladder cancer, renal cancer, bladder cancer, prostate cancer, testicular cancer, cervical cancer, endometrial cancer, choriocarcinoma, ovarian cancer, breast cancer, thyroid cancer, brain cancer, head and neck cancer, malignant melanoma, skin cancer, liver cancer, leukemia, lymphoma, multiple myeloma, chronic myelogenous leukemia, neuroblastoma, and aplastic anemia, and
   wherein the antitumor agent is selected from the group consisting of paclitaxel, doxorubicin, vincristine, daunorubicin, vinblastine, actinomycin-D, docetaxel, etoposide, teniposide, bisantrene, homoharringtonine, Gleevec (STI-571), cisplatin, 5-fluorouracil, adriamycin, methotrexate, busulfan, chlorambucil, cyclophosphamide, melphalan, nitrogen mustard, and nitrosourea.

4. A pharmaceutical composition for treating stroke comprising:
   (i) an isolated polypeptide consisting of the sequence (I) Cys-X1-Val-Ala-Pro-X2; and
   (ii) an anti-stroke agent bound to the polypeptide of (i) as an effective ingredient;
   wherein X1 is an amino acid with polar uncharged side chain and X2 is an amino acid with positive charged side chain, and
   wherein the anti-stroke agent is selected from the group consisting of streptokinase, urokinase, and alteplase.

5. A pharmaceutical composition for treating myocardial infarction comprising:
   (i) an isolated polypeptide consisting of the sequence (I) Cys-X1-Val-Ala-Pro-X2; and
   (ii) an anti-myocardial infarction agent bound to the polypeptide of (i) as an effective ingredient;
   wherein X1 is an amino acid with polar uncharged side chain and X2 is an amino acid with positive charged side chain, and
   wherein the anti-myocardial infarction agent is selected from the group consisting of streptokinase, urokinase, alteplase, angiotensin II inhibitor, aldosterone receptor inhibitor, erythropoietin, and NMDA (N-methyl-D-aspartate) receptor inhibitor.

6. A pharmaceutical composition for treating arteriosclerosis comprising:
   (i) an isolated polypeptide consisting of the sequence (I) Cys-X1-Val-Ala-Pro-X2; and
   (ii) an anti-arteriosclerosis agent bound to the polypeptide of (i) as an effective ingredient,
   wherein X1 is an amino acid with polar uncharged side chain and X2 is an amino acid with positive charged side chain, and
   wherein the anti-arteriosclerosis agent is selected from the group consisting of lovastatin, rapamycin, Celebrex, Ticlopin, Marimastat, and Trocade.

7. A method for drug delivery comprising administering the composition of claim 3 to a subject in need thereof at an effective dose.

8. A method for treating neoplastic disease comprising administering the pharmaceutical composition of claim 3 to a subject in need thereof at an effective dose.

9. A method for treating stroke comprising administering the pharmaceutical composition of claim 4 to a subject in need thereof at an effective dose.

10. A method for treating myocardial infarction comprising administering the pharmaceutical composition of claim 5 to a subject in need thereof at an effective dose.

11. A method for treating arteriosclerosis comprising administering the pharmaceutical composition of claim 6 to a subject in need thereof at an effective dose.

12. A method for imaging a disease site selected from the group consisting of neoplastic disease, stroke, myocardial infarction and arteriosclerosis comprising administering the composition of claim 1 to a subject in need thereof at an effective dose.

13. The composition of claim 1, wherein the amino acid with polar uncharged side chain is Ser or Thr.

14. The composition of claim 1, wherein the amino acid with positive charged side chain is Arg or Lys.

15. The composition of claim 1, wherein the isolated polypeptide is selected from the group consisting of SEQ ID NO: 2 and SEQ ID NOs: 10 to 12.

* * * * *

SEQUENCE LISTING

```
<160> NUMBER OF SEQ ID NOS: 14

<210> SEQ ID NO 1
<211> LENGTH: 6
<212> TYPE: PRT
<213> ORGANISM: Artificial Sequence
<220> FEATURE:
<223> OTHER INFORMATION: Peptide 1 for targeting apoptotic cells

<400> SEQUENCE: 1

Cys Gln Arg Pro Pro Arg
1               5

<210> SEQ ID NO 2
<211> LENGTH: 6
<212> TYPE: PRT
<213> ORGANISM: Artificial Sequence
```

```
<220> FEATURE:
<223> OTHER INFORMATION: Peptide 2 for targeting apoptotic cells

<400> SEQUENCE: 2

Cys Ser Val Ala Pro Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Peptide 3 for targeting apoptotic cells

<400> SEQUENCE: 3

Cys Asn Arg Pro Pro Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Peptide 4 for targeting apoptotic cells

<400> SEQUENCE: 4

Cys Gln Lys Pro Pro Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Peptide 5 for targeting apoptotic cells

<400> SEQUENCE: 5

Cys Gln Arg Pro Pro Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Peptide 6 for targeting apoptotic cells

<400> SEQUENCE: 6

Cys Asn Lys Pro Pro Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Peptide 7 for targeting apoptotic cells

<400> SEQUENCE: 7

Cys Asn Arg Pro Pro Lys
1               5

<210> SEQ ID NO 8
<211> LENGTH: 6
<212> TYPE: PRT
<213> ORGANISM: Artificial Sequence
```

```
<220> FEATURE:
<223> OTHER INFORMATION: Peptide 8 for targeting apoptotic cells

<400> SEQUENCE: 8

Cys Gln Lys Pro Pro Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Peptide 9 for targeting apoptotic cells

<400> SEQUENCE: 9

Cys Asn Lys Pro Pro Lys
1               5

<210> SEQ ID NO 10
<211> LENGTH: 6
<212> TYPE: PRT
<213> ORGANISM: Artificial Sequence
<220> FEATURE:
<223> OTHER INFORMATION: Peptide 10 for targeting apoptotic cells

<400> SEQUENCE: 10

Cys Thr Val Ala Pro Arg
1               5

<210> SEQ ID NO 11
<211> LENGTH: 6
<212> TYPE: PRT
<213> ORGANISM: Artificial Sequence
<220> FEATURE:
<223> OTHER INFORMATION: Peptide 11 for targeting apoptotic cells

<400> SEQUENCE: 11

Cys Ser Val Ala Pro Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Peptide 12 for targeting apoptotic cells

<400> SEQUENCE: 12

Cys Thr Val Ala Pro Lys
1               5

<210> SEQ ID NO 13
<211> LENGTH: 20
<212> TYPE: DNA
<213> ORGANISM: Artificial Sequence
<220> FEATURE:
<223> OTHER INFORMATION: Forward primer

<400> SEQUENCE: 13
agcggaccag attatcgcta                                              20

<210> SEQ ID NO 14
<211> LENGTH: 20
<212> TYPE: DNA
<213> ORGANISM: Artificial Sequence
```

```
<220> FEATURE:
<223> OTHER INFORMATION: Reverse primer

<400> SEQUENCE: 14
aacccctcaa gacccgttta                                                  20
```